US006620604B1

(12) United States Patent
Genicot et al.

(10) Patent No.: US 6,620,604 B1
(45) Date of Patent: Sep. 16, 2003

(54) SULFOHYDROLASES, CORRESPONDING AMINO ACID AND NUCLEOTIDE SEQUENCES, SULFOHYDROLASE PREPARATIONS, PROCESSES, AND PRODUCTS THEREOF

(75) Inventors: Sabine Genicot, Saint Pol de Leon (FR); Bernard Kloareg, Plouenan (FR); Phillipe Potin, Roscoff (FR); Brian Rudolph, Køge (DK); Gerhard De Ruiter, Ede (NL); Bea Penninkhof, Epse (NL); Odile Richard, Teille (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 0 days.

(21) Appl. No.: 09/567,003

(22) Filed: May 9, 2000

Related U.S. Application Data

(60) Provisional application No. 60/133,376, filed on May 10, 1999.

(51) Int. Cl.$^7$ .............................. C12N 9/16; C12P 19/04
(52) U.S. Cl. ........................................ 435/196; 435/101
(58) Field of Search ................................. 435/196, 101

(56) References Cited

U.S. PATENT DOCUMENTS

| | | | | |
|---|---|---|---|---|
| 5,585,255 A | * | 12/1996 | Tsukada et al. | 435/196 |
| 5,932,211 A | * | 8/1999 | Wilson et al. | 424/94.6 |
| 5,939,289 A | | 8/1999 | Ertesvåg et al. | 435/72 |
| 6,001,627 A | | 12/1999 | Dörreich et al. | 435/260 |
| 6,013,504 A | | 1/2000 | Yu et al. | 435/232 |
| 6,037,159 A | | 3/2000 | Uchimura et al. | 435/193 |
| 6,063,915 A | | 5/2000 | Hansen et al. | 536/114 |

FOREIGN PATENT DOCUMENTS

| | | |
|---|---|---|
| FR | 9612204 | 4/1998 |
| FR | 9701148 | 4/1998 |
| WO | 00/06609 | 2/2000 |

OTHER PUBLICATIONS

Armisen et al., "Production, Properties and Uses of Agar", *Production and Utilization of Products from Commercial Seaweeds*, FAO Fisheries Technical Paper, 288, pp. 1–57 (1987).
Stanley, "Production, Properties and Uses of Carrageenan", *Production and Utilization of Products from Commercial Seaweeds*, FAO Fisheries Technical Paper, 288, pp. 116–146 (1987).
Therkelsen, "Carrageenan", *Industrial Gums: Polysaccharides and their Derivatives*, 3rd ed., pp. 145–180, (1993).
DeRuiter et al., "Carrageenan Biotechnology", *Trends in Food Science & Technology*, vol. 8, pp. 389–395 (1997).
Hoffmann et al., "Effect of Isolation Procedures on the Molecular Composition and Physical Properties of *Eucheuma Cottonii* Carrageenan", *Food Hydrocolloids*, 9, pp. 281–289 (1995).

Viebke et al., "Characterization of Kappa– and Iota–Carrageenan Coils and Helices by MALLS/GPC", *Carbohydr. Polym.*, vol. 27, pp. 145–154 (1995).
Le Questel et al., "Computer Modelling of Sulfated Carbohydrates: Applications to Carrageenans", *Int. J. Biol. Macromol.*, vol. 17, pp. 161–174 (1995).
Rees, "Enzymic Synthesis of 3:6–Anyhdro–L–Galactose within Porphyran from L–Galactose 6–Sulphate Units", *Biochem. J.*, 81, pp. 347–352 (1961).
Rees, "Enzymatic Desulphation of Porphyran", *Biochem. J.*, 80, pp. 449–453 (1961).
Wong et al., "Sulfohydrolase Activity and Carrageenan Biosynthesis in *Chondrus crispus* (Rhodophyceae)", *Plant Physiology*, vol. 61, pp. 663–666 (1978).
Zinoun et al., "Evidence of Sulfohydrolase Activity in the Red Alga *Calliblepharis jubata*", *Botanica Marina*, vol. 40, pp. 49–53 (1997).
Lawson et al., "An Enzyme for the Metabolic Control of Polysaccharide Conformation and Function", *Nature*, vol. 227, pp. 392–393 (Jul. 25, 1970).
Craigie et al., "Carrageenan Biosynthesis", *Proc. Int. Seaweed Symp.*, pp. 369–377 (1979).

(List continued on next page.)

*Primary Examiner*—Charles L. Patterson, Jr.
(74) *Attorney, Agent, or Firm*—Greenblum & Bernstein, P.L.C.

(57) ABSTRACT

A purified sulfohydrolase having a purity level based on total amount of protein of at least about 40 wt %. Isolated nucleic acid sequence and amino acid sequences. A process for purifying at least one sulfohydrolase, including subjecting an extract from seaweed to fractionation to obtain fractions; and subjecting at least one of the fractions to phenyl sepharose chromatography to obtain sepharose fractions containing at least one sulfohydrolase. An enzymatically modified compound which has been modified by an isolated sulfohydrolase having a purity level based on total amount of protein of at least about 40 wt %. A process of enzymatically modifying a sulfated compound, including combining at least one sulfohydrolase, having a purity level based on total amount of protein of at least about 40 wt %, with a sulfated compound form a reaction mixture; and incubating the reaction mixture to remove sulfate groups from the sulfated compound to form an enzymatically modified compound. A process of enzymatically modifying a sulfated compound, including incubating a first sulfohydrolase with a sulfated compound to remove sulfate groups from the sulfated compound to form an intermediate compound; and subsequently incubating the intermediate compound with a second sulfohydrolase to remove sulfate groups to form an enzymatically modified compound. A method for extracting one of nu- and mu-carrageenan from seaweed, including dispersing seaweed in a salt solution including $K_2CO_3$ to form a dispersion; filtering the dispersion to obtain a liquid; ultrafiltering the dispersion to remove salts; concentrating the liquid; adjusting the pH of the liquid to about 8 to 8.5; and precipitating one of nu- and mu-carrageenan from the liquid.

9 Claims, No Drawings

OTHER PUBLICATIONS

Selby et al., "Agar", *Industrial Gums: Polysaccharides and their Derivatives,* 3rd ed., pp. 87–103 (1993).

Jol et al., "A Novel High–Performance Anion–Exchange Chromatographic Method for the Analysis of Carrageenans and Agars Containing 3,6–Anhydrogalactose", *Analytical Biochemistry,* 268, pp. 213–222 (1999).

Merril et al., "Ultrasensitive Stain for Proteins on Polyacrylamide Gels Shows Regional Variation in Cerebrospinal Fluid Proteins", *Science,* 211, pp. 1437–1438 (1981).

Laemmli, *Nature,* 277, pp. 680–685 (1970).

Apt et al., "The Gene Family Encoding the Fucoxanthin Chlorophyll Proteins from the Brown Alga *Macrocystis pyrifera*", *Mol. Gen. Genet.,* 246, pp. 455–464 (1995).

Vallon et al., "cDNA Sequence of M(Alpha), the Catalytic Subunit of the *Chlamydomonas reinhardtii* L–Amino Acid Oxidase (Accession No. U78797): a New Sequence Motif Shared by a Wide Variety of Flavoproteins", *Plant Physiol.,* 115, pp. 1729–1731 (1997).

Potin et al., "Purification and Characterization of a New κ–Carrageenase from a Marine Cytophaga–like Bacterium", *Eur. J. Biochem.,* 201, pp. 241–247 (1991).

Kidby et al., "A Convenient Ferricyanide Estimation of Reducing Sugars in the Nanomole Range", *Analytical Biochemistry,* 55, pp. 321–325 (1973).

Knutsen et al., "The Use of Neocarrabiose Oligosaccharides with Different Length and Sulphate Substitution as Model Compounds for $^1$H–NMR Spectroscopy", *Carbohydrate Research,* 299, pp. 233–244 (1992).

Falshaw et al., "Structural Analysis of Carrageenans from Burmese and Thai Samples of *Cantenella nipae Zanardini*", *Carbohydrate Research,* 285, pp. 81–98 (1996).

Stortz et al., "High–Field NMR Spectroscopy of Cystocarpic and Tetrasporic Carrageenans from *Irideae undulosa*", *Carbohydrate Research,* 261, pp. 317–326 (1994).

Hemmingson et al., "Biosynthesis of Agar Polysaccharides in *Gracilaria chilensis* Bird, McLachlan et Oliveira", *Carbohydrate Research,* 287, pp. 101–115 (1996).

Hemmingson et al., "In Vivo Conversion of 6–O–sulfo–L–galactopyranosyl Residues into 3,6–anhydro–L–galactopyranosyl Residues in *Gracilaria chilensis* Bird, McLachlan et Oliveira", *Carbohydrate Research,* 296, pp. 285–292 (1996).

Peat et al., "Carbohydrase and Sulphatase Activities of *Porphyra umbilicalis*", *Biochem. J.,* 79, pp. 7–12 (1961).

"Carrageenan, General Description" (Product Literature of Hercules Incorporated), pp. 1–20 (Feb. 1996).

Bradford, "A Rapid and Sensitive Method for the Quantitation of Microgram Quantities of Protein Utilizing the Principle of Protein–Dye Binding", *Anal. Biochem.,* 72, pp. 248–254 (1976).

Knutsen et al., "Characterisation of Water–Extractable Polysaccharides from Norwegian *Furcellaria Lumbricalis* (Huds.) Lamour. (Gigartinales, Rhodophyceae) by IR and NMR Spectroscopy", *Bot. Mar.,* 30, pp. 497–505 (1987).

Craigie et al., "Carrageenans and Agars", *Handbook of Phycological Methods, Biochemical and Physiological Methods,* pp. 109–131 (1978).

Falshaw et al., "The Backbone of the Sulfated Galactan from *Plocamium costatum* (*C Agardh*) Hook. f. et Harv. (Plocamiaceae, Rhodophyta)", *Bot. Mar.,* 42, pp. 431–435 (1999).

Usov et al., "Polysaccharides of Algae. XXXIV: Detection of Iota–Carrageenan in *Phyllophora brodiaei* (Turn.) J. Ag. (Rhodophyta) Using $^{13}$C–NMR Spectroscopy", *Botanica Marina,* 28, pp. 367–373 (1985).

Renn, "Biotechnology and the Red Seaweed Polysaccharide Industry: Status, Needs, and Prospects", *Tibtech,* 15, 9–14 (1997).

Rees, "Structure, Conformation, and Mechanism in the Formation of Polysaccharide Gels and Networks", *Adv. Carbohydr. Chem. Biochem.,* 24, pp. 267–332 (1969).

Grasdalen et al, "Iodide–Specific Formation of κCarrageenan Single Helices. $^{127}$I NMR Spectroscopic Evidence for Selective Site Binding of Iodide Anions in the Ordered Conformation", *Macromolecules,* 14, 1842–1845 (1981).

Rochas et al., "Mechanisms of Gel Formation in κ–Carrageenan", *Biopolymers,* 23, pp. 735–745 (1984).

La Claire II et al., "An Autoradiographic and Histochemical Localization of Sulfated Polysaccharides in *Eucheuma nudum* (Rhodophyta)", *J. Phycol.,* 12, pp. 368–375 (1976).

Craigie et al., "Carrageenan Biosynthesis", *Proc. Intern. Seaweed Symposium,* 9, pp. 369–377 (1979).

McLean et al., "Neocarratetraose 4–O–Monosulphate β–Hydrolase from *Pseudomonas carrageenovora*", *Eur. J. Biochem.,* 113, pp. 447–456 (1981).

Shaw et al., "Substrate Specificity and Other Properties of the Inducible S3 Secondary Alkylsulphohydrolase Purified from the Detergent–Degrading Bacterium Pseudomonas C12B", *Biochem. J.,* 187, pp. 181–196 (1980).

\* cited by examiner

SEQUENCE LISTING

<160> NUMBER OF SEQ ID NOS: 23

<210> SEQ ID NO 1
<211> LENGTH: 25
<212> TYPE: PRT
<213> ORGANISM: Chondrus crispus

<400> SEQUENCE: 1

Lys Glu Gly Cys Glu Thr Ala Ile Val Gly Ala Gly Ile Gly Ala
1               5                   10                  15

Tyr Ser Ala Phe Arg Leu Ala Ser Pro
            20                  25

<210> SEQ ID NO 2
<211> LENGTH: 14
<212> TYPE: PRT
<213> ORGANISM: Chondrus crispus

<400> SEQUENCE: 2

Gly Leu Ile Gly Leu Asn Asn Leu Val Thr Pro Met Glu Lys
1               5                   10

<210> SEQ ID NO 3
<211> LENGTH: 17
<212> TYPE: PRT
<213> ORGANISM: Chondrus crispus

<400> SEQUENCE: 3

Met Ser Gly Val Glu Gln Val Tyr Phe Asp Asp Leu His Ala Gln Ile
1               5                   10                  15

Lys

<210> SEQ ID NO 4
<211> LENGTH: 17
<212> TYPE: PRT
<213> ORGANISM: Chondrus crispus

<400> SEQUENCE: 4

Glu Ile Arg Asp Arg Val Glu Glu Leu Glu Lys Glu Glu Asp Tyr Ala
1               5                   10                  15

Lys

<210> SEQ ID NO 5
<211> LENGTH: 11
<212> TYPE: PRT
<213> ORGANISM: Chondrus crispus

<400> SEQUENCE: 5

Gly Arg Thr Asn Val Tyr Glu Leu Tyr Ala Lys
1               5                   10

<210> SEQ ID NO 6
<211> LENGTH: 11
<212> TYPE: PRT
<213> ORGANISM: Chondrus crispus

<400> SEQUENCE: 6

Trp Val Val Asn Ile Val Ile Asn Gly Val Arg
1               5                   10

<210> SEQ ID NO 7

```
<211> LENGTH: 11
<212> TYPE: PRT
<213> ORGANISM: Chondrus crispus

<400> SEQUENCE: 7

Gln Val Leu Glu Leu Glu Phe Thr Val Val Arg
1               5                   10

<210> SEQ ID NO 8
<211> LENGTH: 8
<212> TYPE: PRT
<213> ORGANISM: Chondrus crispus

<400> SEQUENCE: 8

Leu Ser Pro Leu Thr Phe Gln Arg
1               5

<210> SEQ ID NO 9
<211> LENGTH: 16
<212> TYPE: PRT
<213> ORGANISM: Chondrus crispus
<220> FEATURE:
<221> NAME/KEY: UNSURE
<222> LOCATION: (9)..(9)
<223> OTHER INFORMATION: any amino acid

<400> SEQUENCE: 9

Ile Asn Asp Asn Leu Val Tyr Gln Xaa Gly Asn Leu Pro Ala Gly Lys
1               5                   10                  15

<210> SEQ ID NO 10
<211> LENGTH: 13
<212> TYPE: PRT
<213> ORGANISM: Chondrus crispus

<400> SEQUENCE: 10

Asn Tyr Asn Ile Gln Asn Thr Asp Gly Ser Val Phe Arg
1               5                   10

<210> SEQ ID NO 11
<211> LENGTH: 6
<212> TYPE: PRT
<213> ORGANISM: Chondrus crispus

<400> SEQUENCE: 11

Met Thr Val Glu Phe Gln
1               5

<210> SEQ ID NO 12
<211> LENGTH: 17
<212> TYPE: PRT
<213> ORGANISM: Chondrus crispus

<400> SEQUENCE: 12

Ala Ala Arg Gly Ala Arg Gly Gly Arg Thr Gly Tyr Gly Ala Arg Ala
1               5                   10                  15

Cys

<210> SEQ ID NO 13
<211> LENGTH: 20
<212> TYPE: PRT
<213> ORGANISM: Chondrus crispus

<400> SEQUENCE: 13

Gly Thr Arg Thr Thr Tyr Thr Gly Asp Ala Thr Arg Thr Thr Arg Thr
```

```
                1               5               10              15
Ala Gly Thr Thr
                20

<210> SEQ ID NO 14
<211> LENGTH: 20
<212> TYPE: PRT
<213> ORGANISM: Chondrus crispus

<400> SEQUENCE: 14

Ala Ala Asn Ala Cys Asn Tyr Trp Asn Cys Cys Arg Thr Cys Ile Gly
1               5                   10                  15

Thr Gly Thr Thr
                20

<210> SEQ ID NO 15
<211> LENGTH: 17
<212> TYPE: DNA
<213> ORGANISM: Chondrus crispus

<400> SEQUENCE: 15
attaaccctc actaaag                                                    17

<210> SEQ ID NO 16
<211> LENGTH: 17
<212> TYPE: DNA
<213> ORGANISM: Chondrus crispus

<400> SEQUENCE: 16
aatacgactc actatag                                                    17

<210> SEQ ID NO 17
<211> LENGTH: 2020
<212> TYPE: DNA
<213> ORGANISM: Chondrus crispus

<400> SEQUENCE: 17
gacagccctc cccaacatgg ggctcaccta cgttcttttg tctgttcttg tcttacaagc       60
aacccacgca cttgccaaag agggatgcga gaccgctata gttggagccg gaattggtgg      120
cgcttattct gccttccgtt tggcaagccc atcagtctgt atctttgaag ccaaccgtcg      180
cccaggaggg cgcatcttga ccgttcggga tccaagcgcc tcgtttctga acttcactat      240
tgaccttggt gcgtatcgct accatcgtgc acaccatcgt cttgtccgcc tcgttgctga      300
agacctactc aaccttcctg tggcttgcta tacggacttg ctcaacaacc gaaaagattg      360
tccggacgcg acgattcgtc tcttttcaac tcgagggaac gtgcttggag ctcttggagg      420
ccggattgct caagacttaa taagaagta cggaccgttc ctgccatatg tgattcagag      480
gagctttcgg tggggacaag gaaagccctt gaaggaaaga cggacaatgt ctgggttgct      540
aatcgggcca aactcagtaa tcaaagagat ccgagatcgc gttgaggagc ttgagaaaga      600
ggaagactat gcgaaagcga tgcagattgc ggacgaaatc attgcggcaa tgcaagatgg      660
ctcgtacaga ggcatcccgt attcagagat cagtttgatg caagtcgcga tccgtgaagg      720
ctttacgaca gaggagatgc aactggaaac ggacttctca tttctcagca gtgtggaaag      780
gcggcagacg ctagaataca acgggcagct ttcaatcagg caaatggcac tagaaaaggg      840
acttataggg cttaacaatc tagtgacgcc gatggagaag cggcgtggag tgctacgtag      900
agcgggcatg atcacgctcg tggacggcct gcttgagcgg gcgatgaagg gcggtgtgca      960
```

-continued

| | |
|---|---|
| ggtacaatat gggaagaagg tcgtgagaat tacgcgcacc ggaaatgaga agaggcctat | 1020 |
| aagactcaag ttcgaggacg gcgggatggt agaagtgaag aacgtgattc tcaacattgg | 1080 |
| caagccgggg ctgattgctc ttgggctgga ctcggagccg atgatgagca ccaaggagcc | 1140 |
| tttccggcga gcggtcgagc gaaactttgt gctgagctta ccaagacgt attgtttctg | 1200 |
| ggaagacgcg tggtggttga caaagttggg gcaacgggat gggcgtattc aggttccttc | 1260 |
| agattcgatg cagtcaatgc gataccacga tggacacgtc gtgtgcaagg acgagagaag | 1320 |
| gcttaaaagt tgccgtggcg gattgctcgc gtcgtactcg gggggcgatc agatgggct | 1380 |
| tggggctgct ttgcatgcgc acgtgcataa tgctaaaccg tacacaccgc tgacaagcag | 1440 |
| tgacaacgta gtgaaattga ttccagggaa gatgtctgga gtagagcaag tatactttga | 1500 |
| tgacctgcac gcacaaatca agcgtgtgca caagaggtcg gtggagcgga aggggcttga | 1560 |
| cgtggacaag gtgatttcca agccggctat gtgcctattt gcggattggc gggaggtggg | 1620 |
| tactcatgcg gccatggggc cgggaaaagg aagaacgaat gtgtacgagt tgtacgctaa | 1680 |
| accggttagt gatttgagaa tcgcactggt aaacgaagcg tggagtgggg accaaggtg | 1740 |
| ggcggagggg agcttgagaa gcgcagagcg ggcgctgttc caccaattcg gaatggagaa | 1800 |
| gccagagtgg atggataagg agtatcaccg gtcggtgatt gagaggtaca accagggtg | 1860 |
| atttcggcgc gggcatacag tatgcgtgtc gttcgtgaag ttgtagcaaa gggctaatcc | 1920 |
| ttccacctgt cgtctcggcg caaagaataa aagctcgaag attagtggtg acgttagaag | 1980 |
| taggcataca gaaccaaaaa aaaaaaaaaa aaaaaaaaaa | 2020 |

<210> SEQ ID NO 18
<211> LENGTH: 1399
<212> TYPE: DNA
<213> ORGANISM: Chondrus crispus
<220> FEATURE:
<221> NAME/KEY: Unsure
<222> LOCATION: (18)..(18)
<223> OTHER INFORMATION: any nucleotide
<221> NAME/KEY: Unsure
<222> LOCATION: (1315)..(1315)
<223> OTHER INFORMATION: any nucleotide
<221> NAME/KEY: Unsure
<222> LOCATION: (1321)..(1322)
<223> OTHER INFORMATION: any nucleotide
<221> NAME/KEY: Unsure
<222> LOCATION: (1356)..(1356)
<223> OTHER INFORMATION: any nucleotide
<221> NAME/KEY: Unsure
<222> LOCATION: (1360)..(1360)
<223> OTHER INFORMATION: any nucleotide
<221> NAME/KEY: Unsure
<222> LOCATION: (1364)..(1364)
<223> OTHER INFORMATION: any nucleotide
<221> NAME/KEY: Unsure
<222> LOCATION: (1366)..(1366)
<223> OTHER INFORMATION: any nucleotide
<221> NAME/KEY: Unsure
<222> LOCATION: (1372)..(1372)
<223> OTHER INFORMATION: any nucleotide
<221> NAME/KEY: Unsure
<222> LOCATION: (1394)..(1394)
<223> OTHER INFORMATION: any nucleotide

<400> SEQUENCE: 18

| | |
|---|---|
| aaatttaaag gaattttnaa aaaattttaa agcttaaatt tgccatttgc cattaaggtg | 60 |
| ggcaattgtt ggaaagcgat cggttgggcc tttttgtttt tacgcaagct ggaaaagggg | 120 |
| attgtgctcc aaggcgatta agttgggtaa cgcaaggtt ttcccagtca gacgttgtaa | 180 |
| aacgacggcc agtgaattgt aatacgactc actatagggc gaattggta ccgggccccc | 240 |

-continued

```
cctcgagttt tttttttttt ttttttttca gaggcgaaag gtgtcgttta ctgaaatctc      300
aagtacggga gcaactccgc ccatctctac tcatcgttca ctacaagttg cagacactat      360
ttcacgctca tcacgaggta agggaaacgg tactcgatac ctttactcac tcctcttaga      420
cagtgaactc gagctcaaga acctgcctgc cgtccacgtt cgagcggccc aacctgcgtt      480
caaccctgac tccgttgatc acaatgttga ctacccacct tgtgcggtta ttgaagcagt      540
tgttgaaatg gaacagcttg acagtgtact tccctggaac catgttcgtg aacgacacag      600
cttccttgcc ggccggcaag ttgccgcact ggtacaccaa gttgtcattg atacgtcctc      660
cctgggagcc cggcggccca tcaacggaaa ggtcgaaatc atcggacgaa tcccacgcca      720
cgtccaccac gatcggccgc acaaccgtct ggaatgagag cagtccctg gcgtcggacg      780 tcgcgatcgt gcggaacacg gacccatcgg tgttctgaat gttgtagttg cggatcggaa      840
gacggatgca gaggtcgtcg aggaagtcct cctggttacc cacagggcta cggcgggaga      900 caccctgag ttcgcgctgg aacgtgagag gggaaagacg gaagtagttt ggcgggaacg       960
ggtggctcag tccgtttggc ctgtacctgt tgatgggggt ggtgcgtgag cccgattcaa      1020
cgagggcaac gccagttttg cggatgctgc cgagcgtccg gccgcccggg aagttacggc      1080
agacggatgc ctgcagcccg gggatccac tagttctaga gcggccgcca ccgcggtgga      1140
gctccagctt tgttcccctt tagtgagggt taatttcgag cttggcgtaa tcatggtcat      1200
agctgttttc tgtgtgaaat tggtatccgc tcacaattca cacaacatac cagccccgaa      1260
acataaatgt taaagcctgg gtggctaatg agtgagctta cttacattaa ttggnttggc      1320
nntacttgcc ccttttttaaa tcggggaaac ctttcngccn actntnttaa anaatcggcc      1380 aacccccgg gganagggg                                                    1399
```

<210> SEQ ID NO 19
<211> LENGTH: 1387
<212> TYPE: DNA
<213> ORGANISM: Chondrus crispus

<400> SEQUENCE: 19

```
tttttgccca ttgcccatca aggtgggcaa ttttggaaa ggcgatcggg tggggccttt        60
tggtaattac gcaagctgca aaagggggaat gtgctgcaag ccgattaagt tgggtaacgc     120
cagggttttc ccagtcagaa cgttgtaaac gcgggcagtg aattgtaata cgactcacta     180
tagggcgaat tgggtaccgg gccccccctc gagttttttt tttttttttt tttttttttt     240
tttttttttt tttggagatg aaaggtgtcg tttactgata ccaagtacgg cgcaactccg     300
cccatctcta ctcatcgtca ctacaggttg caaaacactat tccacgacca tgacgattta    360
agggaacgct acttgggacc ttccactcat tcctcttaga cggtgaactc gagctcgaga     420
accctcctgc cgtccacatt cgaccgcccc aacctgcgtt gaattcttac cccgttgacc     480
acaacgttca ccacccactt cgtacgctta ttgaagcagt tgttgaagtg aacagcgtg      540 accgtgtact tccctcgaac catgttttcg aaggacacag cttccttgcc ggccggagag     600
tcgccgcacg cggccaccaa gttgtcattg atacggcctc ctacagatcc agggggacca     660 acaacgaaa ggtcgaagtc atcggacgaa tcccacgcca cgtccaccac gatcggccgc      720
acaaccgtcc ggaatgaaag gcagtccctg gcgtccgacg tcgagatcgt ccggaacaca     780
gtcccatccg tgttctgaat gttgtagttg cggatcggaa gacggatgca gaggtcgtcg     840
aggaactcct cctggttacc catggcgcca cgacgagcga cgcccttgcg gtcgcgctgg     900
```

-continued

```
aatgtcagag gcgtcagacg gaagtagttt ctcgggaacg cgggtctcag tccattaggc      960
cggtacctgt tgatcggcgt ggtgcctgag cctgattcaa tgagcgccgc gccagtggtg     1020
cgaacgttgc cgagcgttct cccgccgggg aagttacggc agatgaatgc tgagcgggag     1080
tagtctggcc cgcggagaag gatcttcgca cccttgggac gcatggagcc atcagcgcgg     1140
cagaagcgga accggcatga gcggccgcat tgcgcgttcg ctgtgaaggc gatagcggcc     1200
aggagaagga cgaacaggaa tgaagcgttc attgttggta tgtgaagact gccgcaccga     1260
aatgaaggct gctggtgccg aattcctgca gcccggggga tccactagtt ctagagcggc     1320
cgccaccgcg gtggagctcc agcttttgtt cccttagtg agggttaatt tcgagcttgg     1380
cgtaatg                                                                1387
```

<210> SEQ ID NO 20
<211> LENGTH: 1460
<212> TYPE: DNA
<213> ORGANISM: Chondrus crispus

<400> SEQUENCE: 20

```
atctcgaaat taaccctcac taaagggaac aaaagctgga gctccaccgc ggtggcggcc       60
gctctagaac tagtggatcc cccgggctgc aggaattcgg caccagcagc cttcatttcg      120
gtgcggcagt cttcacatac caacaatgaa cgcttcattc ctgttcgtcc ttctcctggc      180
cgctatcgcc ttcacagcga acgcccaatg cggccgctca tgccggttcc gcttctgccg      240
cgctgatggc tccatgcgtc ccaagggtgc gaaggtcctt ctccgcgggc cagactactc      300
ccgctcagca ttcatctgcc gtaacttccc tggcgggaga acgctcggca acgttcgcac      360
cactggcgcg gcgctcattg aatcaggctc aggcaccacg ccgatcaaca ggtaccggcc      420
caatggactg agacccgcgt tcccgagaaa ctacttccgt ctgacgcctc tgacattcca      480
gcgcgaccgc aagggcgtcg ctcgtcgtgg cgccatgggg aaccaggagg agttcctcga      540
cgacctctgc atccgtcttc cgatccgcaa ctacaacatt cagaacaagg atgggtctgt      600
gttccggacg atctcgacgt cggacgccag ggactgcctt tcattccgga cggttgtgcg      660
gccgatcgtg gtggacgtgg cgtgggattc gtccgatgac ttcgaccttt ccgttgttgg      720 tcccccctgga tctgtaggag gccgtatcaa tgacaacttg gtggccgcgt gcggcgactc      780
tccggccggc aaggaagctg tgtccttcga aaacatggtt cgagggaagt acacggtcac      840
gctgttccac ttcaacaact gcttcaataa gcgtacgaag tgggtggtga acgttgtggt      900
caacggggta aggattcaac gcaggttggg gcggtcgaat gtggacggca ggagggttct      960
cgagctcgag ttcaccgtct aagaggaatg agtggaaggt cccaagtagc gttcccttac     1020
atcgtcatgg tcgtggaata gtgtttgcaa cctgtagtga cgatgagtag agatgggcgg     1080
agttgcgccg cacttggtat cagtaaacga caccttcat ctctgttcga aaaaaaaaa      1140 aaaaaaaact cgagggggggg cccggtaccc aattcgccct atagtgagtc gaattacaat     1200
tcactggccg cgttttacaa cgtcgtgact gggaaaaccc tcgttaccc aacttaatcg     1260 ctttgaagac aatccctttt tccaacttgg ggtaaaaacc aaagggccc gcaccattcg      1320 cctttccaaa aatttgccca cccttaatgg caaaatggca aattttaagc cttaaatttt     1380
ttttaaaaat tcccgttaaa tttttttaaa ataacttatt ttttaaccaa ataggcccaa     1440
atcgggaaaa tccctttaa                                                   1460
```

<210> SEQ ID NO 21
<211> LENGTH: 1068

<210> SEQ ID NO 21
<211> LENGTH: 1068
<212> TYPE: DNA
<213> ORGANISM: Chondrus crispus

<400> SEQUENCE: 21

| | | | | | |
|---|---|---|---|---|---|
| gaattcggca | cgagcagcct | tcatttcggt | gcggcagtct | tcacatacca | acaatgaacg | 60 |
| cttcattcct | gttcgtcctt | ctcctggccg | ctatcgcctt | cacagcgaac | gcccaatgcg | 120 |
| gccgctcatg | ccggttccgc | ttctgccgcg | ctgatggctc | catgcgtccc | aagggtgcga | 180 |
| agatccttct | ccgcgggcca | gactactccc | gctcagcatt | catctgccgt | aacttccccg | 240 |
| gcgggagaac | gctcggcaac | gttcgcacca | ctggcgcggc | gctcattgaa | tcaggctcag | 300 |
| gcaccacgcc | gatcaacagg | taccggccca | atggactgag | acccgcgttc | ccgagaaact | 360 |
| tcttccgtct | gacgcctctg | acattccagc | gcgaccgcaa | gggcgtcgct | cgtcgtggcg | 420 |
| ccatgggtaa | ccaggaggag | ttcctcgacg | acctctgcat | ccgtcttccg | atccgcaact | 480 |
| acaacattca | gaacaaggat | gggtctgtgt | tccggacgat | ctcgacgtcg | gacgccaggg | 540 |
| actgcctttc | attccggacg | gttgtgcggc | cgatcgtggt | ggacgtggcg | tgggattcgt | 600 |
| ccgatgactt | cgacctttcc | gttgttggtc | ccctggatc | tgtaggaggc | cgtatcaatg | 660 |
| acaacttggt | ggccgcgtgc | ggcgactctc | cggccggcaa | ggaagctgtg | tccttcgaaa | 720 |
| acatggttcg | agggaagtac | acggtcacgc | tgttccactt | caacaactgc | ttcaataagc | 780 |
| gtacgaagtg | ggtggtgaac | gttgtggtca | acggggtaag | gattcaacgc | aggttggggc | 840 |
| ggtcgaatgt | ggacggcagg | agggttctcg | agctcgagtt | caccgtctaa | gaggaatgag | 900 |
| tggaaggtcc | caagtagcgt | tcccttacat | cgtcatggtc | gtggaatagt | gtttgcaacc | 960 |
| tgtagtgacg | atgagtagag | atgggcggag | ttgcgccgca | cttggtatca | gtaaacgaca | 1020 |
| cctttcatct | ctgttcgaaa | aaaaaaaaa | aaaaaaaaa | aactcgag | | 1068 |

<210> SEQ ID NO 22
<211> LENGTH: 614
<212> TYPE: PRT
<213> ORGANISM: Chondrus crispus

<400> SEQUENCE: 22

Met Gly Leu Thr Tyr Val Leu Leu Ser Val Leu Val Leu Gln Ala Thr
1               5                   10                  15

His Ala Leu Ala Lys Glu Gly Cys Glu Thr Ala Ile Val Gly Ala Gly
                20                  25                  30

Ile Gly Gly Ala Tyr Ser Ala Phe Arg Leu Ala Ser Pro Ser Val Cys
            35                  40                  45

Ile Phe Glu Ala Asn Arg Arg Pro Gly Gly Arg Ile Leu Thr Val Arg
        50                  55                  60

Asp Pro Ser Ala Ser Phe Leu Asn Phe Thr Ile Asp Leu Gly Ala Tyr
65                  70                  75                  80

Arg Tyr His Arg Ala His His Arg Leu Val Arg Leu Val Ala Glu Asp
                85                  90                  95

Leu Leu Asn Leu Pro Val Ala Cys Tyr Thr Asp Leu Leu Asn Asn Arg
                100                 105                 110

Lys Asp Cys Pro Asp Ala Thr Ile Arg Leu Phe Ser Thr Arg Gly Asn
            115                 120                 125

Val Leu Gly Ala Leu Gly Gly Arg Ile Ala Gln Asp Leu Ile Lys Lys
        130                 135                 140

Tyr Gly Pro Phe Leu Pro Tyr Val Ile Gln Arg Ser Phe Arg Trp Gly
145                 150                 155                 160

-continued

```
Gln Gly Lys Pro Leu Lys Glu Arg Arg Thr Met Ser Gly Leu Leu Ile
            165                 170                 175
Gly Pro Asn Ser Val Ile Lys Glu Ile Arg Asp Arg Val Glu Glu Leu
        180                 185                 190
Glu Lys Glu Glu Asp Tyr Ala Lys Ala Met Gln Ile Ala Asp Glu Ile
    195                 200                 205
Ile Ala Ala Met Gln Asp Gly Ser Tyr Arg Gly Ile Pro Tyr Ser Glu
210                 215                 220
Ile Ser Leu Met Gln Val Ala Ile Arg Glu Gly Phe Thr Thr Glu Glu
225                 230                 235                 240
Met Gln Leu Glu Thr Asp Phe Ser Phe Leu Ser Ser Val Glu Arg Arg
                245                 250                 255
Gln Thr Leu Glu Tyr Asn Gly Gln Leu Ser Ile Arg Gln Met Ala Leu
            260                 265                 270
Glu Lys Gly Leu Ile Gly Leu Asn Asn Leu Val Thr Pro Met Glu Lys
        275                 280                 285
Arg Arg Gly Val Leu Arg Arg Ala Gly Met Ile Thr Leu Val Asp Gly
    290                 295                 300
Leu Leu Glu Arg Ala Met Lys Gly Gly Val Gln Val Gln Tyr Gly Lys
305                 310                 315                 320
Lys Val Val Arg Ile Thr Arg Thr Gly Asn Glu Lys Arg Pro Ile Arg
                325                 330                 335
Leu Lys Phe Glu Asp Gly Gly Met Val Glu Val Lys Asn Val Ile Leu
            340                 345                 350
Asn Ile Gly Lys Pro Gly Leu Ile Ala Leu Gly Leu Asp Ser Glu Pro
        355                 360                 365
Met Met Ser Thr Lys Glu Pro Phe Arg Arg Ala Val Glu Arg Asn Phe
    370                 375                 380
Val Leu Ser Leu Ser Lys Thr Tyr Cys Phe Trp Glu Asp Ala Trp Trp
385                 390                 395                 400
Leu Thr Lys Leu Gly Gln Arg Asp Gly Arg Ile Gln Val Pro Ser Asp
                405                 410                 415
Ser Met Gln Ser Met Arg Tyr His Asp Gly His Val Val Cys Lys Asp
            420                 425                 430
Glu Arg Arg Leu Lys Ser Cys Arg Gly Gly Leu Leu Ala Ser Tyr Ser
        435                 440                 445
Gly Gly Asp Gln Met Gly Leu Gly Ala Ala Leu His Ala His Val His
    450                 455                 460
Asn Ala Lys Pro Tyr Thr Pro Leu Thr Ser Ser Asp Asn Val Val Lys
465                 470                 475                 480
Leu Ile Pro Gly Lys Met Ser Gly Val Glu Gln Val Tyr Phe Asp Asp
                485                 490                 495
Leu His Ala Gln Ile Lys Arg Val His Lys Arg Ser Val Glu Arg Lys
            500                 505                 510
Gly Leu Asp Val Asp Lys Val Ile Ser Lys Pro Ala Met Cys Leu Phe
        515                 520                 525
Ala Asp Trp Arg Glu Val Gly Thr His Ala Ala Met Gly Pro Gly Lys
    530                 535                 540
Gly Arg Thr Asn Val Tyr Glu Leu Tyr Ala Lys Pro Val Ser Asp Leu
545                 550                 555                 560
Arg Ile Ala Leu Val Asn Glu Ala Trp Ser Gly Asp Gln Gly Trp Ala
                565                 570                 575
Glu Gly Ser Leu Arg Ser Ala Glu Arg Ala Leu Phe His Gln Phe Gly
```

-continued

```
                580                 585                 590
Met Glu Lys Pro Glu Trp Met Asp Lys Glu Tyr His Arg Ser Val Ile
            595                 600                 605
Glu Arg Tyr Asn Gln Gly
        610

<210> SEQ ID NO 23
<211> LENGTH: 278
<212> TYPE: PRT
<213> ORGANISM: Chondrus crispus

<400> SEQUENCE: 23

Met Asn Ala Ser Phe Leu Phe Val Leu Asn Leu Ala Ala Ile Ala Phe
1               5                   10                  15

Thr Ala Asn Ala Gln Cys Gly Arg Ser Cys Arg Phe Arg Phe Cys Arg
            20                  25                  30

Ala Asp Gly Ser Met Arg Pro Lys Gly Ala Lys Ile Leu Leu Arg Gly
        35                  40                  45

Pro Asp Tyr Ser Arg Ser Ala Phe Ile Cys Arg Asn Phe Pro Gly Gly
    50                  55                  60

Arg Thr Leu Gly Asn Val Arg Thr Thr Gly Ala Ala Leu Ile Glu Ser
65                  70                  75                  80

Gly Ser Gly Thr Thr Pro Ile Asn Arg Tyr Arg Pro Asn Gly Leu Arg
                85                  90                  95

Pro Ala Phe Pro Arg Asn Phe Phe Arg Leu Thr Pro Leu Thr Phe Gln
            100                 105                 110

Arg Asp Arg Lys Gly Val Ala Arg Arg Gly Ala Asn Gly Asn Gln Glu
        115                 120                 125

Glu Phe Leu Asp Asp Leu Cys Ile Arg Leu Pro Ile Arg Asn Tyr Asn
    130                 135                 140

Ile Gln Asn Lys Asp Gly Ser Val Phe Arg Thr Ile Ser Thr Ser Asp
145                 150                 155                 160

Ala Arg Asp Cys Leu Ser Phe Arg Thr Val Val Arg Pro Ile Val Val
                165                 170                 175

Asp Val Ala Trp Asp Ser Ser Asp Asp Phe Asp Leu Ser Val Val Gly
            180                 185                 190

Pro Pro Gly Ser Val Gly Gly Arg Ile Asn Asp Asn Leu Val Ala Ala
        195                 200                 205

Cys Gly Asp Ser Pro Ala Gly Lys Glu Ala Val Ser Phe Glu Asn Met
    210                 215                 220

Val Arg Gly Lys Tyr Thr Val Thr Leu Phe His Phe Asn Asn Cys Phe
225                 230                 235                 240

Asn Lys Arg Thr Lys Trp Val Val Asn Val Val Val Asn Gly Val Arg
                245                 250                 255

Ile Gln Arg Arg Leu Gly Arg Ser Asn Val Asp Gly Arg Arg Val Leu
            260                 265                 270

Glu Leu Glu Phe Thr Val
        275
```

SULFOHYDROLASES, CORRESPONDING AMINO ACID AND NUCLEOTIDE SEQUENCES, SULFOHYDROLASE PREPARATIONS, PROCESSES, AND PRODUCTS THEREOF

CROSS-REFERENCE TO RELATED APPLICATION

The present application claims the priority under 35 U.S.C. §119(e) of U.S. Provisional Application No. 60/133,376, filed May 10, 1999, the disclosure of which is expressly incorporated by reference herein in its entirety.

BACKGROUND OF THE INVENTION

1. Field of the Invention

The present invention relates to sulfohydrolases, such as galactan sulfohydrolases, such as nu- and mu-carrageenan sulfohydrolases. The present invention is directed to the amino acid and nucleotide sequences of sulfohydrolases. The present invention is further directed to enzymatic modification of sulfated compounds, such as galactans. For example, the enzymatic modification may involve tailoring of the properties of sulfated galactans, such as gelling properties, such as by removal of sulfate groups and creation of a bridge between ring positions in a saccharide structure of the galactan. The present invention is further directed to processes of extracting nu-carrageenan from seaweed. The present invention is also directed to enzymatically modified compounds.

2. Discussion of Background

Hydrocolloids, which may be broadly defined as substances that yield a gel in the presence of water, are used in part for their rheological properties, and may also provide benefits in stability.

There are several classes of hydrocolloids. One categorization approach breaks these classes into exudates, such as gum arabic, ghatti, karaya, talha, and tragacanth; extracts, such as alginate from brown seaweeds, agar, carrageenan, and furcelleran from red seaweeds, and konjak (glucomannan), guar, pectin and arabinogalactan from land plants; biopolymers, such as xanthan; chemically modified hydrocolloids, such as the cellulosics, including carboxymethyl cellulose, hydroxypropyl cellulose, and carboxymethylhydroxymethyl cellulose; and intermediate forms, such as microcrystalline cellulose.

Red seaweeds are known sources of industrial gelling and thickening cell-wall sulfated galactans referred to as agar and carrageenans. They consist of a linear backbone of galactopyranose residues linked by alternating alpha(1→3) and beta(1→4) linkages. While all β-linked residues are in the D-configuration, the alpha(1→4)-linked galactose units are in the L-configuration in agars and in the D-configuration in carrageenans.

Agar is extracted from dried algae by more or less hot alkaline solutions (100–120° C.). After filtration, agar solutions are allowed to gel de-watered by pressing, dried, and ground, as disclosed in ARMISEN et al., "Production, Properties and Uses of Agar", *Production and Utilization of Products from Commercial Seaweeds*, FAO Fisheries Technical Paper, 288, pp. 1–57 (1987), the disclosure of which is herein incorporated by reference in its entirety. Seaweed sources for agar extraction include the genera Gelidium, Pterocladia, Gelidiella, and Gracilaria, as disclosed in STANLEY, "Production, Properties and Uses of Carrageenan", *Production and Utilization of Products from Commercial Seaweeds*, FAO Fisheries Technical Paper, 288, pp. 116–146 (1987), the disclosure of which is herein incorporated by reference in its entirety.

Carrageenan is itself a generic name for a family of natural water-soluble sulfated galactans isolated from red seaweeds. The thickening and gelation properties exhibited by carrageenans are useful in food and cosmetic formulations, as disclosed in THERKELSEN, "Carrageenan", *Industrial Gums: Polysaccharides and their Derivatives*, 3rd ed., pp. 145–180, (1993), and DeRUITER et al., "Carrageenan Biotechnology", *Trends in Food Science & Technology*, Vol. 8, pp. 389–395 (1997), both of which are herein incorporated by reference in their entireties.

Seaweed sources for carrageenan include the genera Eucheuma (such as *E. spinosum*, *E. cottonii* (=*Kappaphycus alvarezii*), and *E. denticulatum*), Chondrus (such as *C. crispus*), Calliblepharis (such as *C. jubata*), and Gigartina (such as *G. radula* and *G. stellata*).

Carrageenans are linear, partially sulfated galactans mainly composed of repeating dimers of an alpha(1–4)-linked D-galactopyranose or 3,6-anhydro-D-galactopyranose residue and a beta(1–3)-linked D-galactopyranose residue. As noted above, agars are likewise linear, partially sulfated galactans of similar structure, except that the alpha(1–4)-linked galactopyranose residue is in the L-form. Carrageenan occurs in several structures that differ primarily in the number and placement of sulfate groups on the dimer backbone, and in whether the individual residues of the dimer are present in the left hand ($^4C_1$) or right-hand ($^1C_4$) 'chair' configuration. These structures include kappa (κ), iota (ι), lambda (λ), theta (θ), mu (μ), and nu (ν), as shown below. The iota-, kappa-, and theta-carrageenans contain 3,6-anhydro bridges, whereas the nu-, mu-, and lambda-carrageenans do not have this bridge. Furthermore, the conformation of the alpha-linked unit of nu-, mu-, and lambda-carrageenans is different from the anhydrobridge-containing carrageenans, preventing sufficient helix aggregation. Helix aggregation is important because helices facilitate formation of gels. In this regard, kappa-carrageenan forms firm, brittle gels, whereas iota-carrageenan forms elastic, soft gels, and whereas lambda-carrageenan is a non-gelling thickening agent.

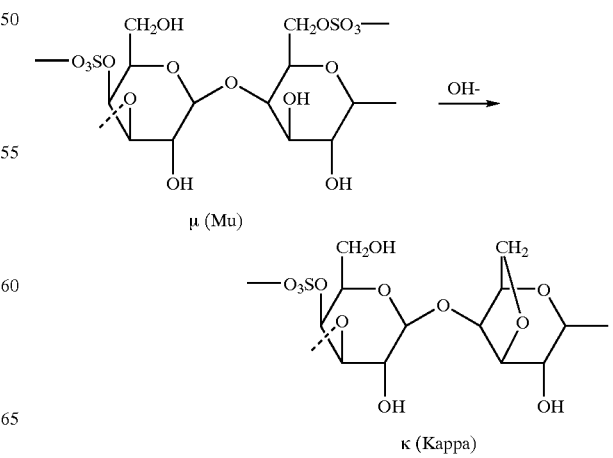

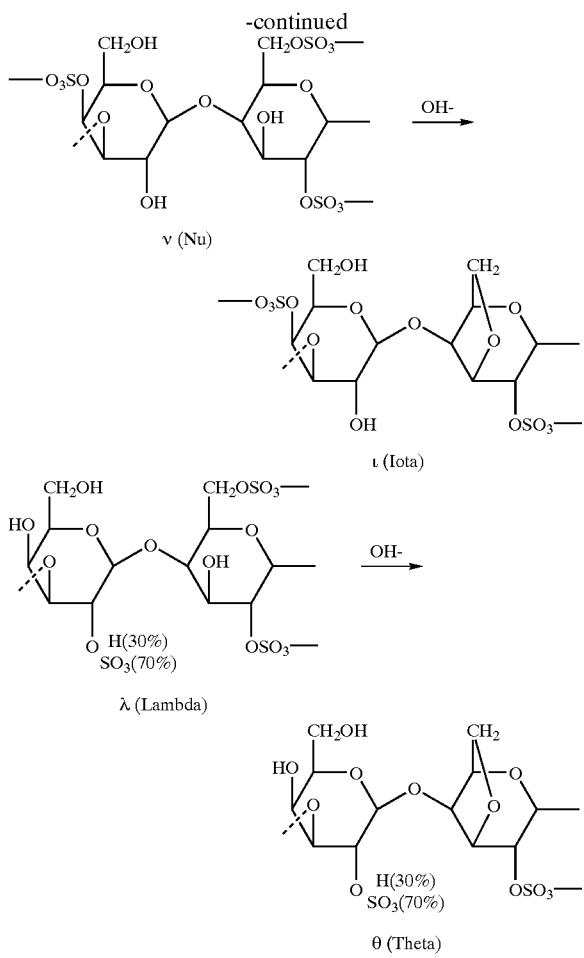

The amount of $SO_3^-$ in carrageenans can be considerable and vary between 0 and 41% (w/w), resulting in highly negatively charged polymers. Ideal kappa-, iota-, and lambda-carrageenan dimers respectively have 1, 2, and 3 sulfate esters groups, resulting in typical sulfate contents of respectively 22%, 32%, and 38% (w/w). However, large variations in sulfate can occur in commercial extracts due to differences in seaweed species or batches. The sulfate ester linkages are chemically very stable, and there are no apparent or practical chemical methods to modify the sulfate level or distribution without also lowering the molecular weight of the polymer, except for the removal of 6-O-sulfate from precursor carrageenans as is done during alkaline treatment.

Carrageenan is typically extracted commercially from red seaweeds by boiling in aqueous solution, sometimes under alkaline conditions, followed by filtration, concentration, precipitation, and drying. Precipitation may either be by alcohol addition, or by gelling with salts followed by pressing of the gel, as discussed in STANLEY, "Production, Properties and Uses of Carrageenan", *Production and Utilization of Products from Commercial Seaweeds*, FAO Fisheries Technical Paper, 288, pp. 116–146 (1987), the disclosure of which is herein incorporated by reference in its entirety. Semi-refined carrageenans are also produced by treating seaweeds with alkali followed by thorough rinsing with water. These treatments improve the gelling characteristics of the carrageenan preparation and remove most of the proteins, pigments and small metabolites; such preparations also contain other polymers such as cellulosic materials, as discussed in HOFFMANN et al., "Effect of Isolation Procedures on the Molecular Composition and Physical Properties of *Eucheuma Cottonii* Carrageenan", *Food Hydrocolloids*, 9, pp. 281–289 (1995), the disclosure of which is herein incorporated by reference in its entirety.

The non-gelling mu- and nu-carrageenans are the natural precursors present in seaweed of, respectively, kappa- and iota-carrageenans, and have a sulfate ester group at the C-6 position of the alpha(1–4)-linked D-galactopyranose residue of the dimeric unit. It has been generally assumed that elimination of the sulfate from the C-6 sulfate ester of the precursors, and formation of the 3,6-anhydro bridge, occur concomitantly during the strong alkaline treatment.

The functional properties (including helix formation, rheological properties, and applications) of the different carrageenans are determined by (1) molecular weight of the polymer (2) the number of sulfate ester groups and their place of substitution of the carbon backbone, and (3) the number of 3,6-anhydro-galactose residues, as discussed in THERKELSEN, "Carrageenan", *Industrial Gums: Polysaccharides and their Derivatives*, 3rd edition, pp. 145–180 (1993); VIEBKE et al., "Characterization of Kappa- and Iota-Carrageenan Coils and Helices by MALLS/GPC", *Carbohydr. Polym.*, Vol. 27, pp. 145–154 (1995); and Le QUESTEL et al., "Computer Modelling of Sulfated Carbohydrates: Applications to Carrageenans", *Int. J. Biol. Macromol.*, Vol. 17, pp. 161–174 (1995), the disclosures of which are herein incorporated by reference in their entireties.

Alkali treatments allow some control over the ratio of carrageenan forms in the final product. However, it is often difficult to predict and obtain the desired final product.

It has been reported that the red seaweed *Porphyra umbilicalis*, contains a "sulfohydrolase" which catalyzes the release of sulfate from porphyran, the major polysaccharide from Porphyra spp. related to agar in that it contains about 10% (w/w) of 3,6-anhydro-L-galactose. It also contains L-galactose-6-sulfate. These latter units can be converted into 3,6-anhydro-L-galactose by the action of an enzyme partially purified from an extract of the parent seaweed as discussed in REES, "Enzymic Synthesis of 3:6-Anhydro-L-Galactose within Porphyran from L-Galactose 6-Sulphate Units", *Biochem. J.*, 81, pp. 347–352 (1961); and REES, "Enzymatic Desulphation of Porphyran", *Biochem. J.*, 80, pp. 449–453 (1961), the disclosures of which are both incorporated herein by reference in their entireties.

It has also been reported that carrageenan-producing red seaweeds contain a "sulfohydrolase" which catalyzes the release of sulfate from carrageenan precursors. The sulfohydrolase in *Chondrus crispus* is discussed in WONG et al., "Sulfohydrolase Activity and Carrageenan Biosynthesis in *Chondrus crispus* (Rhodophyceae)", *Plant Physiology*, Vol. 61, pp. 663–666 (1978), the disclosure of which is herein incorporated by reference in its entirety. The sulfohydrolase in *Calliblepharis jubata* is discussed in ZINOUN et al., "Evidence of Sulfohydrolase Activity in the Red Alga *Calliblepharis jubata*", *Botanica Marina*, Vol. 40, pp. 49–53 (1997), the disclosure of which is herein incorporated by reference in its entirety. The sulfohydrolase in *Gigartina stellata* is discussed in both LAWSON et al., "An Enzyme for the Metabolic Control of Polysaccharide Conformation and Function", *Nature*, Vol. 227, pp. 392–93 (July 25, 1970) and WONG et al., "Sulfohydrolase Activity and Carrageenan Biosynthesis in *Chondrus crispus* (Rhodophyceae)", *Plant Physiology*, Vol. 61, pp. 663–666 (1979), the disclosures of which are herein incorporated by reference in their entireties. Such enzymes have not been previously purified to homogeneity and no electrophoresis data has been provided in previous reports.

The mode of action and degree of specificity of galactan sulfohydrolases have only been described in general terms in the literature. As discussed in CRAIGIE et al., "Carrageenan Biosynthesis", *Proc. Int. Seaweed Symp.*, pp. 369–377 (1978), the disclosure of which is herein incorporated by reference, it is unclear how many sulfohydrolases with different specificity are present in *C. crispus*. In general, there is little discussion in the literature of the chemical structure of the sulfohydrolase substrates, the end-products of enzymatic action, and the extent of action of the sulfohydrolase on the galactan precursor.

Thus, there is a need for a variety of sulfohydrolases with different specificity which can be used to tailor the properties of sulfated compounds, such as galactans.

SUMMARY OF THE INVENTION

The present invention is directed to providing purified sulfohydrolases having various specificities.

The present invention is also directed to amino acid and nucleotide sequences of sulfohydrolases.

The present invention is directed to methods of enzymatically modifying sulfated compounds.

The present invention is additionally directed to methods of extracting carrageenan from seaweed.

The present invention is further directed to sulfated compounds, such as galactans, which have been modified with sulfohydrolases, such as to modify gelling properties.

In accordance with one aspect, the present invention is directed to sulfohydrolase having a purity level based on total amount of protein of at least about 40 wt %. The purity level may also be at least about 70 wt %, at least about 90 wt %, or at least about 95 wt %.

In accordance with another aspect, the present invention is directed to an isolated nucleic acid sequence comprising a sequence of SEQ ID NO: 17.

In accordance with yet another aspect, the present invention is directed to an isolated nucleic acid sequence comprising a sequence having at least about 25% homology with SEQ ID NO: 17. The homology with SEQ ID NO: 17 may also be at least about 50%, at least about 80%, or at least about 90%.

In accordance with still another aspect, the present invention is directed to an isolated nucleic acid sequence which will hybridize under hybridization conditions with a nucleic acid of SEQ ID NO: 17.

In accordance with another aspect, the present invention is directed to an isolated nucleic acid sequence comprising a sequence of SEQ ID NO: 18.

In accordance with yet another aspect, the present invention is directed to an isolated nucleic acid sequence comprising a sequence of SEQ ID NO: 19.

In accordance with another aspect, the present invention is directed to an isolated nucleic acid sequence comprising a sequence of SEQ ID NO: 20.

In accordance with another aspect, the present invention is directed to an isolated nucleic acid sequence comprising a sequence of SEQ ID NO: 21.

In accordance with yet another aspect, the present invention is directed to an isolated nucleic acid sequence comprising a sequence having at least about 25% homology with SEQ ID NO: 18. The homology with SEQ ID NO: 18 may also be at least about 50%, at least about 80%, or at least about 90%.

In accordance with another aspect, the present invention is directed to an isolated nucleic acid sequence comprising a sequence having at least about 90% homology with SEQ ID NO: 19.

In accordance with still another aspect, the present invention is directed to an isolated nucleic acid sequence comprising a sequence having at least about 90% homology with SEQ ID NO: 20.

In accordance with another aspect, the present invention is directed to an isolated nucleic acid sequence comprising a sequence having at least about 90% homology with SEQ ID NO: 21.

In accordance with yet another aspect, the present invention is directed to an isolated nucleic acid sequence which will hybridize under hybridization conditions with a nucleic acid of SEQ ID NO: 18.

In accordance with another aspect, the present invention is directed to an isolated nucleic acid sequence encoding for an amino acid sequence corresponding to SEQ ID NO: 22.

In accordance with yet another aspect, the present invention is directed to an isolated protein comprising an amino acid sequence comprising SEQ ID NO: 22.

In accordance with still another aspect, the present invention is directed to an isolated protein comprising an amino acid sequence which has at least about 35% homology with SEQ ID NO: 22. The homology with SEQ ID NO: 22 may also be at least about 50% or at least about 80%.

In accordance with yet another aspect, the present invention is directed to an isolated nucleic acid sequence encoding for an amino acid sequence corresponding to SEQ ID NO: 23.

In accordance with another aspect, the present invention is directed to an isolated protein comprising an amino acid sequence comprising SEQ ID NO: 23.

In accordance with yet another aspect, the present invention is directed to an isolated protein comprising an amino acid sequence which has at least about 20% homology with SEQ ID NO: 23. The homology with SEQ ID NO: 23 may also be at least about 50% or at least about 80%.

In accordance with a further aspect, the present invention is directed to a process for purifying at least one sulfohydrolase, comprising: subjecting an extract from seaweed to fractionation to obtain fractions; and subjecting at least one of the fractions to phenyl sepharose chromatography to obtain sepharose fractions containing at least one sulfohydrolase.

In accordance with still another aspect, the present invention is directed to an enzymatically modified compound which has been modified by an isolated sulfohydrolase having a purity level based on total amount of protein of at least about 40 wt %. The purity of the isolated sulfohydrolase may be at least about 70 wt %, at least about 90 wt %, or at least about 95 wt %.

In accordance with a further aspect, the present invention is directed to a process of enzymatically modifying a sulfated compound, comprising: combining at least one sulfohydrolase, having a purity level based on total amount of protein of at least about 40 wt %, with a sulfated compound to form a reaction mixture; and incubating the reaction mixture to remove sulfate groups from the sulfated compound to form an enzymatically modified compound.

In accordance with still another aspect, the present invention is directed to a process of enzymatically modifying a sulfated compound, comprising: incubating a first sulfohydrolase with a sulfated compound to remove sulfate groups from the sulfated compound to form an intermediate compound; and subsequently incubating the intermediate compound with a second sulfohydrolase to remove sulfate groups to form an enzymatically modified compound.

In accordance with another aspect, the present invention is directed to a product made by incubating a sulfated compound with a solution having a protein content consisting essentially of a sulfohydrolase which removes sulfate groups processively.

In accordance with still another aspect, the present invention is directed to a product made by incubating a sulfated compound with a solution having a protein content consisting essentially of a sulfohydrolase which removes sulfate groups randomly.

In accordance with yet another aspect, the present invention is directed to a method for extracting one of nu- and mu-carrageenan from seaweed, comprising: dispersing seaweed in a salt solution comprising $K_2CO_3$ to form a dispersion; filtering the dispersion to obtain a liquid; ultrafiltering the dispersion to remove salts; concentrating the liquid; adjusting the pH of the liquid to about 8 to 8.5; and precipitating the one of nu- and mu-carrageenan from the liquid.

In one aspect, the sulfohydrolase is capable of removing sulfate from hydrocolloid. The hydrocolloid may be one of glycosaminoglycan, fucan, and galactan. In other words, the sulfohydrolase hydrolyzes ester-sulfate bonds present in hydrocolloids.

In another aspect, the sulfohydrolase is capable of removing sulfate from galactan.

In another aspect, the galactan comprises carrageenan. The carrageenan may comprise mu-carrageenan, e.g., comprising at least about 50 mol % mu-carrageenan. The carrageenan may comprise nu-carrageenan, e.g., comprising at least about 50 mol % nu-carrageenan.

In another aspect, the galactan comprises agar.

In yet another aspect, the sulfohydrolase comprises 6-O-sulfohydrolase.

In still another aspect, the sulfohydrolase is capable of converting nu-carrageenan into iota-carrageenan.

In another aspect, the sulfohydrolase is capable of converting mu-carrageenan into kappa-carrageenan.

In another aspect, the sulfohydrolase is capable of removing 6-O-sulfate to induce anhydrobridge formation.

In another aspect, the fractionation comprises ammonium sulfate fractionation.

In still another aspect, the method further comprises subjecting at least one of the phenyl sepharose fractions to DEAE sepharose chromatography to obtain DEAE sepharose fractions. At least one of the DEAE sepharose fractions may be subjected to heparin sepharose chromatography.

In another aspect, the incubation is at a temperature of about 0 to 60° C.

In still another aspect, the incubation is at a pH of about 5.5 to 9.5.

In yet another aspect, the at least one sulfohydrolase to be added to the reaction mixture is contained within a solution having a concentration of the at least one sulfohydrolase of at least about 2 to 85 µg/ml.

In another aspect, the sulfated compound is at a concentration of about 0.012 to 2% (w/v) in the reaction mixture.

In yet another aspect, the modified compound comprises iota-carrageenan.

In still another aspect, the modified compound comprises kappa-carrageenan.

In another aspect, the enzymatically modified compound comprises precursor enriched kappa-carrageenan.

In another aspect, the enzymatically modified compound comprises precursor enriched iota-carrageenan.

In another aspect, the removal of sulfate comprises removing 6-sulfate group from a galactan.

In still another aspect, the removal of sulfate comprises converting nu-carrageenan to iota-carrageenan to form a product that does not gel under conditions wherein the product has a concentration of about 0.7% (w/v) in an aqueous solution having 0.1 M of potassium at a temperature of 40° C. and a pH of 7.

In another aspect, the first sulfohydrolase removes sulfate randomly.

In yet another aspect, the second sulfohydrolase removes sulfate processively.

In another aspect, the seaweed comprises Spinosum.

In still another aspect, the seaweed is freeze-dried and milled prior to being dispersed in the salt solution.

In yet another aspect, the salt solution further comprises KCl. The KCl may have a concentration of about 1 to 1.5 M.

In another aspect, the dispersion is allowed to sit for at least about 18 hours prior to filtering.

In another aspect, the concentrating is by a factor of about 2 to 3.

In still another aspect, the adjusting of the pH of the liquid is by adding base.

In another aspect, the precipitating is by adding isopropyl alcohol.

In yet another aspect, the dialyzing is conducted until the conductivity of the water is stabilized at less than about 2 µS/cm.

In another aspect, after the precipitating of the dialyzed one of nu- and mu-carrageenan, the one of nu- and mu-carrageenan is freeze-dried and milled.

In another aspect, the precipitated dialyzed one of nu- and mu-carrageenan has a one of nu- and mu-content of about 18 to 35 mol %.

In another aspect, the precipitated dialyzed one of nu- and mu-carrageenan has a molecular weight of about 700 to 800 kDa.

DETAILED DESCRIPTION OF THE INVENTION

The particulars shown herein are by way of example and for purposes of illustrative discussion of the various embodiments of the present invention only and are presented in the cause of providing what is believed to be the most useful and readily understood description of the principles and conceptual aspects of the invention. In this regard, no attempt is made to show details of the invention in more detail than is necessary for a fundamental understanding of the invention, the description taken with the drawings making apparent to those skilled in the art how the several forms of the invention may be embodied in practice.

All percent measurements in this application, unless otherwise stated, are measured by weight/volume based upon grams per milliliter. Thus, for example, 30% represents 30 grams out of every 100 milliliters of the sample.

Unless otherwise stated, a reference to a compound or component, includes the compound or component by itself, as well as in combination with other compounds or components, such as mixtures of compounds.

Before further discussion, a definition of the following terms will aid in the understanding of the present invention.

"Galactan": a polysaccharide composed of galactose units and additional units; such as agars and carrageenans. Galactans have at least 50 mol % of galactose units.

"Hydrocolloid": a hydrophilic polysaccharide or derivative, e.g., plant polysaccharide, that swells to produce a viscous dispersion or solution when added to water.

"Hybridization conditions": nucleic acid of interest is transferred onto Nylon membranes, available from Amersham Pharmacia Biotech AB, as described in SAMBROOK et al., *Molecular Cloning: A Laboratory Manual*, 2nd ed., CSH Laboratory Press, Cold Spring Harbor, N.Y. (1989), the disclosure of which is herein incorporated by reference in its entirety. The membranes are hybridized overnight in 6×SSC, 5×Denhar't, 0.1% SDS and 100 µg/ml of salmon sperm DNA at 42° C. In this regard, SSC is an aqueous solution of 3 M sodium chloride and 0.3 M sodium citrate made in accordance with the procedure described in SAMBROOK et al., *Molecular Cloning: A Laboratory Manual*, 2nd ed., CSH Laboratory Press, Cold Spring Harbor, N.Y. (1989), the disclosure of which is herein incorporated by reference in its entirety. After hybridization, filters were washed at 42° C. for 15 minutes in the following solutions, 2×SSC, 0.1% SDS; 1×SSC, 0.1% SDS and exposed to photostimulated screen, available from Molecular Dynamics, Uppsala, Sweden, scanned using Storm, also available from Molecular Dynamics, Uppsala, Sweden.

To determine the percent identity or percent homology of two amino acid sequences or of two nucleic acid sequences, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions).times.100). Preferably, the two sequences are the same length.

The determination of percent homology between two sequences can be accomplished using a mathematical algorithm. A preferred, non-limiting example of a mathematical algorithm utilized for the comparison of two sequences is the algorithm of KARLIN et al., *Proc. Natl. Acad. Sci. USA*, 87, pp. 2264–2268 (1990), the disclosure of which is herein incorporated by reference in its entirety, modified as in KARLIN et al., *Proc. Natl. Acad. Sci. USA*, 90, pp. 5873–5877 (1993), the disclosure of which is herein incorporated by reference in its entirety. Such an algorithm is incorporated into the NBLAST and XBLAST programs of ALTSCHUL et al., *J. Mol. Biol.*, 215, pp. 403–410 (1990), the disclosure of which is herein incorporated by reference in its entirety. BLAST nucleotide searches can be performed with the NBLAST program, score=100, wordlength=12 to obtain nucleotide sequences homologous to sulfohydrolase nucleic acid molecules of the invention. BLAST protein searches can be performed with the XBLAST program, score=50, wordlength=3 to obtain amino acid sequences homologous to sulfohydrolase protein molecules of the invention. To obtain gapped alignments for comparison purposes, Gapped BLAST can be utilized as described in ALTSCHUL et al., *Nucleic Acids Res.*, 25, pp. 3389–3402 (1997), the disclosure of which is herein incorporated by reference in its entirety. Alternatively, PSI-Blast can be used to perform an iterated search which detects distant relationships between molecules. Id. When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of MYERS et al., *CABIOS*, 4, pp. 11–17 (1988), the disclosure of which is herein incorporated by reference in its entirety. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

As an overview, the present invention relates to the isolation and purification of sulfohydrolases. For instance, the sulfohydrolases may be purified from seaweed. The sulfohydrolases are preferably those which are able to remove sulfate from sulfated compounds, such as carrageenan. The sulfohydrolases may also be able to form 3,6-anhydro bridges on the sulfated compounds, e.g., carrageenan. The present invention also relates to methods of enzymatic modification of sulfated compounds. The present invention is further directed to modified sulfated compounds, such as modified carrageenans, such as nu-carrageenan which has been modified to at least have portions which correspond to iota-carrageenan, or such as mu-carrageenan which has been modified to at least have portions which correspond to kappa-carrageenan. The present invention is also directed to methods of extracting carrageenan from seaweed.

Given the guidance in the present application and the current state of the art of: (1) protein purification and (2) partial amino acid sequence determination; (3) construction and use of probes to locate corresponding DNA sequencing; and (4) cloning and sequencing, the discussion which follows makes it possible to (1) isolate the sulfohydrolases; (2) identify their amino acid sequences; (3) construct probes for the corresponding DNA sequences; and (4) identify, isolate, purify, and determine the DNA sequences encoding the enzymes. See, for example, SAMBROOK et al., *Molecular Cloning: A Laboratory Manual*, 2nd ed., CSH Laboratory Press, Cold Spring Harbor, N.Y. (1989), the disclosure of which is herein incorporated by reference in its entirety.

The compounds to be enzymatically modified by the present invention include sulfated compounds. The sulfated compounds include galactans, glycosaminoglycans, and fucans.

Fucans are highly heterogeneous sulfated polysaccharides composed of different sugar residues, such as fucose, galactose, mannose, and uronic acid. The number of fucan groups and their compositional patterns differ considerably. Fucans are produced in brown algae and in Echinoderm. In this regard, fucans may be from the matricial phase of the cell walls of brown algae, which primarily contain L-fucose. L-fucose residues are often linked by alpha(1→3) linkages and sulfated on the C4 position. Enzymatic modification of fucan may affect the anti-coagulating properties of fucans.

Glycosaminoglycans (GAGs) is a family of sulfated polysaccharides from the extracellular matrix of animals, which encompasses, heparin, heparin sulfate, chondroitin sulfate, dermatan sulfate, and keratan sulfate. GAGs consist of disaccharide repeating units containing hexuronic acid and hexosamine. Heparin and heparin sulfate are variably sulfated glucosaminoglycans that consists primarily of alternating alpha(1→4)-linked residues of D-iduronate-2-sulfate or D-glucuronate-2-sulfate and N-sulfo-D-glucosamine-6-sulfate. Enzymatic modification of heparin may affect the anti-clotting properties of heparin. Chondroitin sulfate and dermatan sulfate consist primarily of alternating alpha (1→4)-linked residues of D-iduronate or D-glucuronate and N-sulfo-D-galactosamine-6-sulfate. Usually the C2 or C4 position of the N-acetylgalactosamine is sulfated and the C2 position of iduronic acid in dermatan sulfate is also frequently sulfated. Keratan sulfate disaccharide consists of galactose and N-acetylglucosamine. The C6 position of either the galactose or the N-acetylglucosamine can be sulfated.

Galactans may be obtained from many different sources. For example, galactans may be obtained from seaweed. Examples of galactans include carrageenan and agar.

As an example, the extraction of agar from seaweed is known. For instance, the extraction of agar from seaweeds is described in SELBY et al., "Agar", *Industrial Gums: Polysaccharides and their Derivatives*, 3rd ed., (1993), the disclosure of which is herein incorporated by reference in its entirety.

The extraction of carrageenan from seaweeds is known. For instance, the extraction of carrageenan from seaweeds is described in THERKELSEN, "Carrageenan", *Industrial Gums: Polysaccharides and their Derivatives*, 3rd ed., (1993), the disclosure of which is herein incorporated by reference in its entirety.

The present invention is also directed to a method for extracting higher than natural levels of nu- and mu-carrageenan with high molecular weight, i.e., above about 500 kDa. Depending upon the carrageenan to be extracted, the source for carrageenan may be a seaweed, e.g., *Spinosum, Cottonii*, and *Gigartina radula*.

The seaweed may be freeze-dried, milled, and dispersed in an aqueous KCl solution having a concentration of preferably about 0.05 to 0.3 M, more preferably about 0.1 to 0.15 M, and most preferably about 0.125 M KCl. The dispersion also contains $K_2CO_3$ at a concentration of preferably about 0.0005 to 0.003 M, more preferably about 0.001 to 0.0015 M, and most preferably about 0.00125 M to maintain an alkaline environment, i.e., a pH of preferably about 7 to 9, more preferably about 7.5 to 8.5, and most preferably about 7.8 to 8.3. The corresponding calcium salts, i.e., chlorides and carbonates, may also be used, but since the solubility of these is relatively poor, potassium salts are preferred.

The dispersion is allowed to sit for a period of time, preferably about 1 to 72 hours, more preferably about 16 to 32 hours, and most preferably about 24 hours, at a temperature of about 5 to 55° C., more preferably about 20 to 50° C., and most preferably about room temperature.

After this period of time, the dispersion is filtered. For example, filtration may be conducted with a pressurized kieselguhr-filter.

After filtration, the liquid is preferably ultrafiltered and/or diafiltered, e.g., with an MWCO-membrane of 30 kDa, to remove excess salts. Late in the ultrafiltration, washing of the extract is preferably done by addition of tap water at room temperature. The washing is preferably done until conductivity is below 2 mS/cm and stable. The liquid is preferably concentrated on the ultrafiltration to 25 to 30%. The pH is preferably adjusted to about 8 to 8.5 with, e.g., 0.1 M NaOH.

The liquid is then evaporated to preferably about 10 to 90%, more preferably about 30 to 70%, and most preferably about 50%. For instance, the liquid may be evaporated on a vacuum evaporator.

After evaporation, the pH is adjusted to preferably about 7 to 9, more preferably about 7.5 to 8.5, and most preferably about 8. For instance, the pH may be adjusted to about 8 by adding 1 M NaOH. The carrageenan is then precipitated using isopropyl alcohol (IPA), e.g., 100% (v/v) IPA, available from BP Chemicals Ltd., UK and freeze-dried.

The resulting extract has an enriched nu- or mu-content of preferably about 15 to 40 mol %, more preferably about 17 to 30 mol %, and most preferably about 19 to 24 mol %. The resulting extract also has a high molecular weight of preferably about 500 to 1100 kDa, more preferably about 600 to 900 kDa, and most preferably about 700 to 800 kDa.

The sulfohydrolases of the present invention may be isolated from seaweeds producing sulfated galactans, such as the families of Solieriaceae (such as Eucheuma, Kappaphycus), Gigartinaceae (such as Chondrus, Gigartina), Furcellariaceae, Hypneaceae, Phyllophoraceae, Cystocloniaceae (such as Calliblepharis), and Bangiaceae (such as Porphyra). For example, a non-exhaustive list of seaweed sources and potential seaweed sources for sulfohydrolases include *Eucheuma spinosum, Eucheuma cottonii* (=*Kappaphycus alvarezii*), *Eucheuma denticulatum, Chondrus crispus, Calliblepharis jubata, Gigartina radula, Gigartina stellata*, and *Porphyra umbilicalis*.

The following paragraphs describe techniques for isolating the enzyme. From the guidance and examples of purification techniques described in the present application, a skilled artisan would be able to develop additional techniques for isolating the sulfohydrolases.

To isolate sulfohydrolases in accordance with the present invention, it is often preferred that potential enzyme sources, e.g., seaweeds, be screened for enzyme activity to ensure that an enzyme of interest is present in the potential enzyme source. As discussed in more detail below, the screening typically involves obtaining a crude extract from the potential enzyme source. The crude extract would then be used to treat a variety of substrates under a variety of conditions to generally determine the activity of any enzymes present in the crude extract. With this information, a skilled artisan would be able to generally determine whether it might be worthwhile to subject the potential enzyme source to more thorough purification, as discussed below, and to generally determine conditions under which an enzyme is stable and active.

As an example of a crude extraction technique, to isolate enzymes from *C. crispus*, gametophyte plants of *C. crispus* may be frozen in liquid nitrogen and ground to a powder. Although the powder may be used immediately, to maintain the integrity of enzymes in the powder, the powder may be kept at a low temperature, such as −20° C. to −80° C. until further use.

This powder may then be extracted with a buffer, e.g., 4 volumes of 50 mM Tris-HCl buffer (pH 9.5) containing 10 mM 2-mercaptoethanol and 500 mM KCl. After centrifugation, the supernatant may then be fractionated with cold (e.g., −20° C.) acetone, e.g., in a two step process: (1) from 0 to 30% saturation; and (2) from 30 to 60% saturation of acetone. After each fractionation step, a centrifugation is preferably performed, e.g., at 4° C. for 30 min.

at 10,000×g. The pellets may be dissolved in a buffer, e.g., 2 ml of 50 mM Tris-HCl buffer (pH 7.1) containing 10 mM 2-mercaptoethanol. The pellets as well as an aliquot of the supernatants may then be dialyzed, e.g., overnight at 4° C. against 3×3 liters of 50 mM Tris-HCl buffer (pH 7.1) containing 10 mM 2-mercaptoethanol using a Spectra/por membrane MWCO 6-8000 or 3500, available from Spectrum Laboratories, Inc., Rancho Dominguez, Calif., USA. The pellets and the supernatants may be used to search for sulfohydrolase activity.

As another example of a crude extraction technique, to isolate enzyme from E. cottonii (=Kappaphycus alvarezii), Cottonii may be frozen in liquid nitrogen. The cottonii may be used immediately or kept at low temperature, e.g., −80° C., until further use. Prior to extraction the Cottonii may be ground to a fine powder.

All of the following steps may be performed at 4° C., unless otherwise noted. The powder may then be subjected to extraction using a buffer, e.g., 50 mM Tris-HCl (pH 9.5)+500 mM KCl and 10 mM 2-mercaptoethanol. The resulting suspension may be stirred, e.g., overnight, and then centrifuged, e.g., at 10,000×g for 75 min. using a Beckman J2-21, Rotor JA20 available from Beckman Instruments, Inc., Fullerton, Calif., USA. The supernatant may be fractionated with cold acetone as described previously. After centrifugation, supernatant and pellets are collected. Pellets, as well as an aliquot of the supernatant may then be dialyzed, e.g., using an MWCO 6-8000 or 3500 dialysis membrane available from Spectrum Laboratories, Inc., Rancho Dominguez, Calif., USA, for 20 hours against 4×1 liter of 50 mM Tris-HCl (pH 7.1)+10 mM 2-mercaptoethanol. After dialysis, the supernatant and the redissolved pellets may be used to search for sulfohydrolase.

Once a crude extract is obtained, to determine whether an extract has any sulfohydrolase activity, several assays are possible. For instance, sulfohydrolases remove sulfate groups from carrageenan such that measuring the level of free sulfate is an indication of sulfohydrolase activity. 6-O-sulfohydrolases, which are able to remove 6-O-sulfate, also tend to cause the formation of 3,6-anhydrogalactose bridges and to induce, therefore, an increase of viscosity. Therefore, measuring the level of 3,6-anhydrogalactose bridges is another measure of sulfohydrolase activity. Additionally, 6-O-sulfohydrolase activity corresponds with an increase in viscosity such that viscosity may be measured to indicate sulfohydrolase activity.

Regarding the measuring of free sulfate, the activity of the sulfohydrolases on carrageenans is measured in the present application by a new assay for measuring the free sulfate. Several assays for the determination of free sulfate have been described in the literature, but these assays are either time consuming or not sensitive enough. See WONG et al., "Sulfohydrolase Activity and Carrageenan Biosynthesis in Chondrus crispus (Rhodophyceae)", Plant Physiology, Vol. 61, pp. 663–666 (1978); REES, "Enzymatic Desulphation of Porphyran", Biochem. J., 80, pp. 449–453 (1961); and ZINOUN et al., "Evidence of Sulfohydrolase Activity in the Red Alga Calliblepharis jubata", Botanica Marina, Vol. 40, pp. 49–53 (1997), the disclosures of which are herein incorporated by reference in their entireties.

The new assay for determining free sulfate levels is based on the determination of the free sulfate by high performance anion exchange chromatography using auto suppressed conductivity detection within 8 minutes. Besides being fast and fully automated, this method has the advantage of being reproducible and sensitive since as few as 10 ppm of free sulfate can be easily detected.

For instance, sulfohydrolase activity may be assayed by measuring the amount of sulfate released upon incubation of the enzyme extract on carrageenan. The reaction mixture may contain 100 μl of enzyme sample in 50 mM Tris-HCl (pH 7.1)/10 mM 2-mercaptoethanol and 100 μl of 1.4% (w/v) carrageenan. In this regard, the carrageenan is either in the same buffer or in MilliQ water, available from Millipore Corporation, Bedford, Mass., USA. It should be noted that the enzyme sample may be obtained by any appropriate technique, such as the crude extraction techniques described above. The sample, however, may be any other sample for which a measure of the activity is desired. Unless otherwise noted, a reference mixture is made using enzyme extract boiled for 10 minutes prior to use. After 6 to 15 hours incubation at 48° C., carrageenan is removed from the reaction mixture by centrifugation at 3320×g for 1 hr at 30° C. in a Microcon-10 unit, available from Amicon Bioseparations, Millipore Corporation, Bedford, Mass., USA.

The amount of free sulfate present in the filtrate from the Microcon-10 unit is then analyzed by HPAEC (high performance anion exchange chromatography) using a Dionex DX 500 chromatography system equipped with a GP40 gradient pump and an ED40 electrochemical detector, all available from Dionex Corporation, Sunnyvale, Calif., USA. The column, an IonPac AS12 A anion exchange column (4×200 mm, also available from Dionex Corporation) was mounted on an AG12 Guard column (4×50 mm, also available from Dionex Corporation). The eluent is 9.5 mM $Na_2CO_3$/0.5 mM $NaHCO_3$ at a flow rate of 1.5 ml/min. Detection of anion is performed by ASRS conductivity using an anion self regenerating suppressor ASRS-1 (4 mm, also available from Dionex Corporation) with an SRS (Self Regenerating Suppressor) current of 50 mA.

Regarding measuring 3,6 anhydrogalactose bridges, another assay may be used. The amount of 3,6 anhydrogalactose bridge produced during the desulfatation reaction is measured in this application using the technique described in JOL et al., "A Novel High-Performance Anion-Exchange Chromatographic Method for the Analysis of Carrageenans and Agars Containing 3,6-Anhydrogalactose", Anallyical Biochemstry 268, pp. 213–222 (1999), the disclosure of which is herein incorporated by reference in its entirety.

Regarding measuring viscosity levels, viscometric measurements may be carried out on the reaction mixtures. The viscosity of the reaction mixture is directly measured using a programmable Brookfield rheometer model DV III, available from Brookfield Engineering Laboratories, Stoughton, Mass., USA, thermostated at 48° C. Measurements are performed with a CP52 spindle for 10 minutes using a shear rate of 120 rpm.

Once a sample has been identified as a potential source for enzymes, e.g., by the above described screening, the sulfohydrolases may be purified to homogeneity in accordance with the present invention. From the guidance and purification techniques described in the present application, a skilled artisan would be able to develop additional purification techniques.

A typical example of the purification of the enzymes from C. crispus is shown and discussed on the following pages; all steps are performed at 4° C. unless otherwise noted:

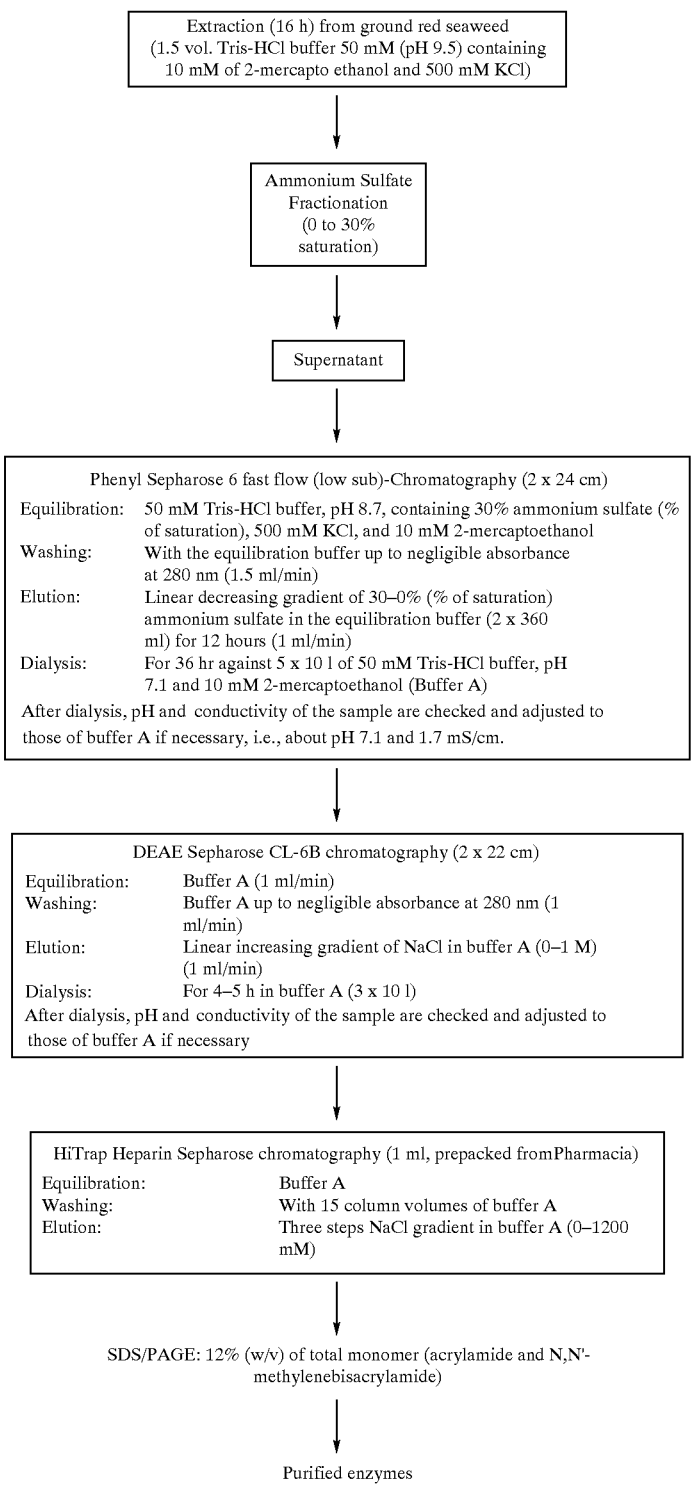

As noted above, all steps of fractionation and purification in the above purification process are performed at 4° C. unless otherwise noted.

Gametophyte plants of *Chondrus crispus* may be frozen in liquid nitrogen and ground. For example, the frozen *C. crispus* may be automatically ground to pieces which are less than 1 mm long by using a Forplex miller, available from Forplex Industrie, Boulogne Billancourt, France. This "powder" may be used immediately or may be kept at low temperature, e.g., −20° C. to −80° C., until further use.

The ground *C. crispus* may then be subjected to extraction. For example, this frozen ground *C. crispus* in the amount of 650 g may be allowed to thaw overnight in 1.5 volumes (v/w) of 4° C. extracting buffer (50 mM Tris-HCl, pH 9.5/500 mM KCl/10 mM 2-Mercaptoethanol). In other words, the 650 g of *C. crispus* may be allowed to thaw in 975 ml of the buffer. The suspension may be stirred overnight and then centrifuged, e.g., at 10,000×g for 75 min.

The supernatant from extraction may then be subjected to fractionation. For instance, the supernatant may be brought to 30% $(NH_4)_2SO_4$ saturation (16.4 g ammonium sulfate/ 100 ml of sample) by adding ammonium sulfate. In this regard, this percentage refers to the percent of saturation in ammonium sulfate which ammonium sulfate solutions are saturated at 3.9 M at 0° C. When all the ammonium sulfate is dissolved, the mixture may be allowed to stand for about 30 min. and then centrifuged, e.g., at 24,700×g for 60 min.

Sulfohydrolase activity usually cannot be detected in the crude extract and sometimes not in the ammonium sulfate supernatant. This property may be the result of interferences with polysaccharides or proteins that are removed during the phenyl sepharose chromatography which is described below. An important purpose of the phenyl sepharose chromatography is to remove phycoerytrin, a hydrophilic protein, which constitutes the major component in the Chondrus extract.

After centrifugation of the ammonium sulfate mixture, the supernatant may be collected and loaded on a phenyl sepharose column, e.g., a Phenyl Sepharose 6 fast flow (2.0×24 cm) column, available from Amersham Pharmacia Biotech AB, Uppsala, Sweden, previously equilibrated in 50 mM Tris-HCl buffer (pH 8.7), 30% $(NH_4)_2SO4$ saturation, 500 mM KCl and 10 mM 2-Mercaptoethanol (buffer D). The column may be washed with this buffer up to negligible absorbance at 280 nm in the effluent. The bound proteins may then be eluted with a linear decreasing gradient of $(NH_4)_2SO_4$ made of 360 ml of buffer D and 360 ml of the same buffer without $(NH_4)_2SO_4$ (buffer C). At the end of the gradient, phycoerythrin as well as some other proteins are often eluted with buffer C alone. As an example, the elution may be conducted under the following conditions:

Buffer D: 50 mM Tris-HCl buffer, pH 8.7, containing 30% of saturation of $(NH_4)_2SO_4$, 500 mM KCl, and 10 mM 2-mercaptoethanol.
Buffer C: 50 mM Tris-HCl buffer, pH 8.7, containing 500 mM KCl, and 10 mM 2-mercaptoethanol.
Flow Rate: 1 ml/min
Fraction Size: 8 ml

| Time (min) | % Buffer D | % Buffer C |
|---|---|---|
| 0 | 100 | 0 |
| 720 | 0 | 100 |

The above described extraction and phenyl sepharose chromatography are preferably performed at least twice in order to have enough material for subsequent steps.

Fractions of interest, i.e., fractions that are later found to have sulfohydrolase activity, from the phenyl sepharose chromatography may then be dialyzed. For instance, active fractions may be pooled and dialyzed for 36 hr against 5×10 1 of 50 mM Tris-HCl buffer (pH 7.1) containing 10 mM 2-Mercaptoethanol (buffer A), using a Spectra/por membrane MWCO 6-8000 or 3500, available from Spectrum Laboratories, Inc., Rancho Dominguez, Calif., USA. After dialysis, the pH and the conductivity of the sample may be checked and adjusted to those of buffer A (i.e., pH 7.1 and conductivity of about 1.7 mS/cm) if necessary.

After dialysis, the sample may then be subjected to DEAE Sepharose chromatography. For instance, the sample may be applied at a flow rate of 1 ml/min to a DEAE Sepharose column (2.0×22 cm), available from Amersham Pharmacia Biotech AB, Uppsala, Sweden, previously equilibrated with buffer A. The column may be washed with buffer A until the absorption at 280 nm is negligible. Then the adsorbed proteins may be eluted, e.g., at a flow rate of 1 ml/min with a linear NaCl (from 0 to 1 M) gradient in buffer A. As an example, the elution may be performed as follows:

Buffer A: 50 mM Tris-HCl buffer, pH 7.1 and 10 mM 2-mercaptoethanol
Buffer B: 50 mM Tris-HCl buffer, pH 7.1 and 10 mM 2-mercaptoethanol+1 M NaCl
Fraction Size: 7.5 ml
Flow Rate: 1 ml/min

| Time (min) | % Buffer A | % Buffer B |
|---|---|---|
| 0 | 100 | 0 |
| 390 | 35 | 65 |
| 450 | 35 | 65 |
| 630 | 0 | 100 |

SDS PAGE analysis of DEAE Sepharose chromatography fractions eluting between 650 and 800 mM NaCl normally reveal the presence of one single band at 34.9 kDa. This band corresponds to an enzyme denoted sulfohydrolase II which is discussed in more detail below.

In addition to sulfohydrolase II, sulfohydrolase I elutes between 300 and 600 mM NaCl during the DEAE chromatography. These fractions, however, usually include impurities as well. To isolate sulfohydrolase I, further purification, such as dialysis and semi-affinity and cation-exchange chromatography, e.g., heparin chromatography, is required.

As an example of heparin chromatography, half of a fraction eluting with 580 mM NaCl may be dialyzed against buffer A using a Spectra/por membrane MWCO 6-8000 or 3500, available from Spectrum Laboratories, Inc., Rancho Dominguez, Calif., USA. The fraction may then be loaded (flow rate 1.5 ml/min) on top of a HiTrap heparin column, available from Amersham Pharmacia Biotech AB, Uppsala, Sweden, previously equilibrated with buffer A. The column may then be washed with this buffer at a flow rate of 1.5 ml/min until the absorbance at 280 nm is negligible. Bound proteins may then be eluted using a three step increasing NaCl gradient (from 0 to 1200 mM). In particular, elution may be conducted using the following gradient:

Buffer A: 50 mM Tris-HCl buffer, pH 7.1 and 10 mM 2-mercaptoethanol
Buffer B': 50 mM Tris-HCl buffer, pH 7.1 and 10 mM 2-mercaptoethanol+1.2 M NaCl
Fraction size: 1.5 ml
Flow rate: 1.5 ml/min

| Time (min) | % Buffer A | % Buffer B' |
|---|---|---|
| 0 | 100 | 0 |
| 10 | 71 | 29 |
| 15 | 71 | 29 |
| 25 | 34 | 66 |
| 30 | 34 | 66 |
| 35 | 0 | 100 |
| 45 | 0 | 100 |

SDS-PAGE analysis of fractions eluting with 1200 mM NaCl should reveal a single faint band characterized by a molecular weight of 62.1 kDa. This band corresponds to an enzyme denoted sulfohydrolase I.

The above-described purification procedure preferably starts with 2×600–700 g of fresh seaweed, such as the above-noted 650 g. With this amount of material, both enzymes separate well after DEAE chromatography, but the sulfohydrolase I is still not pure. The above-described chromatography on semi-affinity and cation exchange chromatography is necessary to purify this enzyme to homogeneity.

Cottonii sulfohydrolases may also be purified using a procedure which is similar to the above procedure for purifying C. crispus sulfohydrolases I and II.

For instance, Cottonii may be frozen in liquid nitrogen and kept at −80° C. until further use. Prior to extraction the frozen Cottonii may be ground, e.g., manually to a fine powder in a mortar, using liquid nitrogen which was poured with a baker into the mortar to keep the Cottonii frozen during the grinding.

To partially purify the Cottonii sulfohydrolase, the following steps may be performed at 4° C. Ground Cottonii may be extracted in buffer, e.g., 25 g of ground Cottonii in 40 ml of 50 mM Tris-HCl (pH 9.5)+500 mM KCl and 10 mM 2-mercaptoethanol. The resulting suspension may be stirred, e.g., with a magnetic stirrer overnight, and then centrifuged, e.g., at 10,000×g for 75 min using a Beckman J2-21, Rotor JA20 available from Beckman Instruments, Inc., Fullerton, Calif., USA. The supernatant may be dialyzed, e.g., using a MWCO 6-8000 or 3500 dialysis membrane available from Spectrum Laboratories, Inc., Rancho Dominguez, Calif., USA, for 20 hours against 4×1 liter of 50 mM Tris-HCl (pH 8.5)+10 mM 2-mercaptoethanol. After dialysis, the supernatant may be loaded on a heparin column, e.g., at a flow rate of 1 ml/min on top of a Heparin agarose type II-S column (27.5×1 cm column, 10×0.5 cm gel size), available from Millipore, Stonehouse, England, with the heparin type II-S agarose gel being available from Sigma Chemical, St. Louis, Mo., USA, previously equilibrated in the same buffer. The column may be washed with this buffer until the absorption at 280 nm is negligible. Then, the adsorbed proteins may be eluted, e.g., for 40 minutes with a linear NaCl (from 0 to 1 M) gradient. In particular, elution may be conducted using the following gradient:

Buffer A: 50 mM Tris-HCl (pH 8.5)+10 mM 2-mercaptoethanol

Buffer B: 50 mM Tris-HCl (pH 8.5)+10 mM 2-mercaptoethanol+1 M NaCl

Fraction size: 2 ml

Flow rate: 1 ml/min

| Time (min) | % of Buffer A | % of Buffer B |
|---|---|---|
| 0 | 100 | 0 |
| 40 | 0 | 100 |

Although most of the proteins in the extract typically do not bind to the heparin agarose, the sulfohydrolase binds to the gel as most of the activity, in terms of sulfate released and/or viscosity increase, is found in later fractions. The fractions from the heparin chromatography may be concentrated, e.g., by about 13×by centrifugation at 3320×g for 1 hr at 4° C. in a Microcon-10 unit, available from Amicon Bioseparations, Millipore Corporation, Bedford, Mass., USA, prior to SDS-PAGE analysis and silver nitrate staining, according to MERRIL et al., "Ultrasensitive Stain for Proteins on Polyacrylamide Gels Shows Regional Variation in Cerebrospinal Fluid Proteins", Science, 211, pp. 1437–1438 (1981), the disclosure of which is herein incorporated by reference in its entirety.

The different active fractions are all characterized by the presence of two common proteins: one which is characterized by a molecular weight of about 65 kDa and another which is characterized by a molecular weight of about 55 kDa.

In accordance with the present invention, based on total weight of protein in the sample, sulfohydrolases may have high purity. The sulfohydrolase is preferably purified to at least about 40 wt %, more preferably at least about 50 wt %, even more preferably at least about 60 wt %, even more preferably at least about 70 wt %, even more preferably at least about 80 wt %, even more preferably at least about 90 wt %, even more preferably at least about 95 wt %, even more preferably at least about 99 wt %, and most preferably 100 wt %, based on total weight of protein. As discussed in more detail below, this high level of purity allows tailoring of the properties of the sulfated compounds to be modified.

Once the sulfohydrolases have been purified, the amino acid sequences may be determined. The peptide sequence of these proteins may be determined by conventional techniques, such as Edman's degradation.

In order to determine the N-terminal amino acid sequence of both sulfohydrolases, the sulfohydrolases were purified generally in accordance with the above-described purification protocol involving extraction, ammonium sulfate fractionation, phenyl sepharose chromatography, DEAE Sepharose chromatography, etc. In particular, fractions 60 and 61 from the DEAE Sepharose chromatography were concentrated 20×, by centrifugation at 3320×g for 1 hr at 4° C. in a Microcon-10 unit, available from Amicon Bioseparations, Millipore Corporation, Bedford, Mass., USA, prior to SDS PAGE. Fractions 38 to 47 from the DEAE chromatography were pooled and dialyzed for 6 hours at 4° C. against 3×3 liters of 50 mM Tris-HCl (pH 7.1)+10 mM 2-mercaptoethanol by using a MWCO 6-8000 or 3500 dialysis membrane available from Spectrum Laboratories, Inc., Rancho Dominguez, Calif., USA. After dialysis, the conductivity of the sample was adjusted to that of the buffer by dilution with milliQ water, available from Millipore Corporation, Bedford, Mass., USA. Half of the sample (57 ml) was then loaded (flow rate 1.5 ml/min) on top of a HiTrap heparin column available from Pharmacia Biotech AB, Uppsala, Sweden, previously equilibrated with 50 mM Tris-HCl (pH 7.1)+10 mM 2-mercaptoethanol. The column was washed with this buffer until the absorbance at 280 nm was negligible. Then, elution of proteins was performed using an increasing gradient (from 0 to 1.2 M) of NaCl. Fractions 24, 25, 26, and 28, which constitute the peak of elution for absorbance at 280 nm, were concentrated about 13×, by centrifugation at 3320×g for 1 hr at 4° C. in a Microcon-10 unit, available from Amicon Bioseparations, Millipore Corporation, Bedford, Mass., USA, before being loaded on a SDS gel for SDS PAGE.

Accordingly, two fractions from the DEAE chromatography (fractions 60 and 61) as well as four fractions from HiTrap Heparin chromatography (fractions 24, 25, 26, and 28), were subjected to SDS PAGE (12% total monomer (acrylamide+N,N'-methylenebisacrylamide) in grams per 100 ml gels) in accordance with the technique described in LAEMMLI, Nature, 227, pp. 680–685 (1970), the disclosure of which is herein incorporated by reference in its entirety, to separate the enzymes.

After SDS PAGE, the proteins were transferred onto a "Hybond-P" membrane (polyvinylidene difluoride (PVDF)

membrane), available from Amersham Pharmacia Biotech AB, Uppsala, Sweden. The transfer was performed for 2 hrs at 250 mA in 50 mM Tris-HCl buffer (pH 8.25) containing 50 mM borate. After transfer, the proteins were then fixed for few seconds in 100% (w/v) methanol and the membrane was then stained for 1 minute with a solution of 0.1% (w/v) Coomassie Blue R250, available from Bio-Rad Laboratories, Hercules, Calif., USA, in 50% (v/v) methanol and 10% (v/v) acetic acid. Destaining is carried out by soaking the membrane for 4–5 minutes in a 50% (v/v) methanol and 10% (v/v) acetic acid solution. After rinsing for 1–2 minutes with MilliQ water, available from Millipore Corporation, Bedford, Mass., USA, the bands corresponding to sulfohydrolases I and II were cut and sent to the Institute Pasteur, Paris, France, for N-terminal amino acid sequence determination by Edman's degradation. From this experiment, it appears that sulfohydrolase II has a blocked amino-terminal end and, therefore, its amino-terminal sequence could not be determined. The Edman's degradation of the sulfohydrolase I resulted in a determination that the N-terminal had the amino acid sequence of SEQ ID NO: 1.

A similar strategy was used to determine the amino acid sequence of some internal peptides. In this case, however, SDS PAGE (12% (total monomer (acrylamide+N,N'-methylenebisacrylamide) in grams per 100 ml gel) gels) in accordance with the technique described in LAEMMLI, Nature, 227, pp. 680–685 (1970), the disclosure of which is herein incorporated by reference in its entirety, was not followed by a transfer. In particular, immediately after electrophoresis, the gel was stained overnight with a 0.0033% (w/v) amido black solution in 50% (v/v) methanol and 10% (v/v) acetic acid. The gel was then briefly rinsed (4×10 min.) with MilliQ water, available from Millipore Corporation, Bedford, Mass., USA, in order to remove traces of methanol and acetic acid. Then, the bands corresponding to sulfohydrolases I and II were excised and dried for about 30 min. at 30° C. in a centrifuged evaporator RC 10.10, Jouan, France, equipped with a refrigerated trap RCT 90, Jouan, France, before being sent to the Institute Pasteur, Paris, France, for proteolytic digestions and microsequence analysis, as discussed below.

Slices of acrylamide, which contained about 15–30 μg of sulfohydrolase I, were submitted to proteolysis with 0.4 μg endoprotease-LysC in 350 μl of 0.05 Tris-HCl (pH 8.6)/ 0.03% (w/v) SDS for 18 h at 37° C. The resulting peptides were then submitted to reverse-phase HPLC on a 250 mm×2.1 mm DEAE C18 column, available from CIL CLUZEAU, Paris, France. Elution, carried out with an acetonitrile gradient from 2 to 45% (v/v) in 0.1% (v/v) trifluoroacetic acid at a flow rate of 0.2 ml/min, allowed many peptides to be separated. Among them, peptides 11, 12, 18, 22, and 25 were significant and were collected for sequencing. These peptides were analyzed at the Institute Pasteur, Paris, France, by Edman's degradation using an Applied Biosystems 473A automated gas phase amino acid sequencer, available from PE Applied Biosystems, Foster City, Calif., USA, in accordance with standard procedures. As a result of this analysis, sulfohydrolase I was determined to include SEQ ID NOS: 2–5.

Acrylamide slices containing about 10 μg of SDS PAGE purified sulfohydrolase II were subjected to proteolysis in 600 μl of 0.05 M Tris-HCl (pH 8.6)/0.01% (v/v) "Tween 20" polyoxyethylene sorbitan monolaurate, available from USB, Cleveland, Ohio, USA, and 4% (w/v) of bovine trypsin. Tryptic digestion was carried out for 18 h at 37° C. The resulting tryptic peptides were purified by reverse-phase HPLC on a 250 mm×2.1 mm DEAE C18 column, available from CIL CLUZEAU, Paris, France. Elution was performed with an acetonitrile gradient from 2 to 45% (v/v) for 60 minutes in 0.1% (v/v) trifluoroacetic acid at a flow rate of 0.2 ml/min. Among the isolated peptides, peptides 13, 14, 24, and 25 were collected because they were the most significant, and were analyzed at the Institute Pasteur, Paris, France, by Edman's degradation using an Applied Biosystems 473A automated gas phase amino acid sequencer, available from PE Applied Biosystems, Foster City, Calif., USA, in accordance with standard procedures. As a result of this analysis, sulfohydrolase I was determined to include SEQ ID NOS: 6–11.

On the basis of the above indicated amino acid sequences, sequence probing processes were carried out for the corresponding cDNA to determine the nucleotide sequence for sulfohydrolase I and II. As described in more detail below, mRNA was isolated from *C. crispus*, from the mRNA a cDNA library was synthesized, the cDNA library was probed with PCR fragments obtained using oligonucleotides based on the above-described amino acid sequences for sulfohydrolase I and II, and positive cDNAs were sequenced.

Total RNA was prepared from gametophytes of *Chondrus crispus* as described by APT et al., "The Gene Family Encoding the Fucoxanthin Chlorophyll Proteins from the Brown Alga *Macrocystis pyrifera*", Mol. Gen. Genet., 246, pp. 455–464 (1995), the disclosure of which is herein incorporated by reference. Purification of the mRNA was then performed using the PolyA T tract mRNA Isolation system IV kit, available from Promega, Madison, Wis., USA, according to the instructions of the manufacturer.

Once the mRNA was isolated, the cDNA library for *C. crispus* was constructed. The cDNA synthesis was performed using a lambda ZAP ®II vector cDNA synthesis kit, available from Stratagene, La Jolla, Calif., USA, according to the instructions of the manufacturer. Double stranded cDNA were fractionated through a sepharose CL-2B column, available from Amersham Pharmacia Biotech AB, Uppsala, Sweden. The fractions with an average size of 600 to 1500 pb, as estimated on acrylamide gel (5%), were selected for the preparation of the library. Ligation of cDNA into lambda ZapII vector as well as transformation of the host strain XL1-Blue MRF' were performed according to the instructions of the manufacturer (Stratagene, La Jolla, Calif., USA).

The probe design and screening protocol for screening the cDNA library was as follows. From SEQ ID NOS: 2 and 10, respectively, degenerated oligonucleotides for sulfohydrolase I and II were designed which correspond to SEQ ID NO: 12 for sulfohydrolase I and SEQ ID NOS: 13–14 for sulfohydrolase II. Degenerated oligonucleotide, SEQ ID NO: 12 was used with vector primer SEQ ID NO: 16 (5'AATACGACTCACTATAG3') to amplify by PCR DNA fragments corresponding to sulfohydrolase I, in the *C. crispus* cDNA library.

Degenerated oligonucleotides, SEQ ID NOS: 13 and 14 were used with vector primer SEQ ID NO: 15 (5'ATTAACCCTCACTAAAG3') to amplify by PCR DNA fragments corresponding to sulfohydrolase II in the *C. crispus* cDNA library as follows. A first PCR using oligonucleotides SEQ ID NO: 14 and SEQ ID NO: 15 gave DNA fragments. Using this first PCR product and oligonucleotides SEQ ID NO: 15 and SEQ ID NO: 13, a DNA fragment corresponding to sulfohydrolase II was amplified.

The cloned PCR fragments corresponding to the sulfohydrolase I gene and the sulfohydrolase II gene were labelled by random priming using the Megaprime kit, available from Amersham Pharmacia Biotech AB, Uppsala, Sweden, and 1850 kBq of $^{32}P$ dCTP, available from Amersham Pharmacia Biotech AB, Uppsala, Sweden. The resulting probes were purified using Sephacryl SR 200, available from Amersham Pharmacia Biotech AB, Uppsala, Sweden, and used to screen the *C. crispus* gametophytes cDNA library.

For both sulfohydrolase I and II screenings, plaques were transferred onto Nylon membranes, available from Amersham Pharmacia Biotech AB, as described in SAMBROOK et al., *Molecular Cloning: A Laboratory Manual*, 2nd ed., CSH Laboratory Press, Cold Spring Harbor, N.Y. (1989), the disclosure of which is herein incorporated by reference in its entirety. The membranes were hybridized overnight in 6×SSC, 5×Denhar't, 0.1% SDS and 100 µg/ml of salmon sperm DNA at 65° C. In this regard, SSC is an aqueous solution of 3 M sodium chloride and 0.3 M sodium citrate made in accordance with the procedure described in SAMBROOK et al., *Molecular Cloning A Laboratory Manual*, 2nd ed., CSH Laboratory Press, Cold Spring Harbor, N.Y. (1989), the disclosure of which is herein incorporated by reference in its entirety. After hybridization, filters were washed 15 minutes in the following solutions, 2×SSC, 0.1% SDS; 1×SSC, 0.1% SDS and 0.4×SSC, 0.1% SDS and exposed to photostimulated screen, available from Molecular Dynamics, Uppsala, Sweden, scanned using Storm, also available from Molecular Dynamics.

For sulfohydrolase I, using the screening conditions described above, the above-described labelled probes for sulfohydrolase I were used in three rounds of screening to screen 300,000 phages from the cDNA library for the presence of sulfohydrolase I cDNA. A total of 408 positive phages (1.4% no %) were positive from which 30 were selected. In a second round, 10 of these positives were screened from which 7 were positive. From these, 6 were found positive in a third round of screening.

For sulfohydrolase II, using the screening conditions described above, the above-described labelled probes for sulfohydrolase II were used in three rounds of screening to screen 600,000 phages from the cDNA library for the presence of sulfohydrolase II cDNA. Twelve positive phages (1/50,000) were found from which 10 were selected. In a second round these positives were screened from which 9 were positive. From these 9, 9 were found positive in a third round of screening. The 5' and 3' extremities of the 9 positive cDNAs were sequenced and sequencing revealed that only 4 of the 9 corresponded to the sulfohydrolase II cDNAs. Thus, the sulfohydrolase II gene seems to be weakly expressed in *C. crispus* gametophyte (1/150,000 cDNAs).

For both sulfohydrolase I and II, in vivo excision was achieved according to the instruction of the manufacturer (packaging kit, available from Stratagene, La Jolla, Calif., USA), and the 5' and 3' termini of each cDNA were sequenced, enabling their identification. In particular, the sequences were determined using the Thermo-Sequenase core sequencing kit with 7-deaza-dGTP from Vistra TM. Sequence reactions were run on a Vistra DNA automated sequencer 725, available from Molecular Dynamics, Uppsala, Sweden.

Using the above method, the sequence of the sulfohydrolase I cDNA was determined to be SEQ ID NO 17. In particular, one cDNA was fully sequenced and the sequence termini were determined for the others. Sequencing revealed that they are identical cDNAs, five are full length cDNAs and one is a partial length cDNA.

The sequence for sulfohydrolase I contains the ATG start codon, the signal peptide (possibly for secretion from the ER to the cell wall) with the probable amino acid cleavage between Alanine 20 and Lysine 21, the stop codon and the 3' UTR (untranslated region).

The above method suggests that the nucleotide sequences for sulfohydrolase II cDNAs are SEQ ID NOS: 18, 19, 20, and 21. In this regard, it is apparent that these 4 cDNAs are different. Three (3) cDNAs are full-length (SEQ ID NOS: 19, 20, and 21) and one may be a partial length cDNA (SEQ ID NO: 18).

From the nucleotide sequences of both sulfohydrolase I and II, the corresponding amino acid sequences were deduced. In particular, the amino acid sequence of sulfohydrolase I was found to be SEQ ID NO: 22. The amino acid sequence of sulfohydrolase II was found to be SEQ ID NO 23.

Regarding the amino acid sequence for sulfohydrolase I, all protein microsequences determined by the Edman's degradation were found in the sequence. The amino acid sequence of sulfohydrolase I has a 20 amino acid long signal peptide. The cleavage site is between Ala 20 and Lys 21. Therefore, the mature enzyme comprises 594 amino acids and contains one potential N-glycosylation site (NFTI; AA 72–75) and has some similarity with the FAD binding domain.

Sulfohydrolase I shares at its C-terminus, 22% of sequence identity over 300 amino acids with the L-amino acid oxidase of *Chlamydomonas reinhardtii*, which was described in VALLON et al., "cDNA Sequence of M(Alpha), the Catalytic Subunit of the *Chlamydomonas reinhardtii* L-Amino Acid Oxidase (Accession No. U78797): a New Sequence Motif Shared by a Wide Variety of Flavoproteins", *Plant Physiol.*, 115, pp. 1729–1731 (1997), the disclosure of which is herein incorporated by reference in its entirety. In this regard, L-amino-acid oxidases have been found in a variety of organisms. They catalyze the reaction: $H_2N—CHR—COOH+O_2+H_2O \rightarrow O=CR—COOH+NH_3+H_2O_2$. In *C. reinhardtii*, it has been shown that this 65 kDa enzyme is periplasmic, gametespecific and induced by ammonium deprivation.

Sulfohydrolase II is 279 amino acids long and contains one glycosylation site. Analysis of sulfohydrolase II sequences indicated that no significant similarity was found with known sequences in the databases available at NCBI (http://www.ncbi.nlm.nih.gov/BLAST/) using BLAST software.

The determination of the amino acid sequences of sulfohydrolase I and II also allows an accurate determination of the molecular weights of these enzymes. In this regard, as estimated by SDS PAGE, the molecular weights of sulfohydrolase I and II are 62.1 and 34.9 kDa, respectively. In the case of the of sulfohydrolase I, this MW is slightly lower than the one deduced from the amino acid sequence which gave a molecular weight of 66.8 kDa. In contrast, relative to the SDS PAGE estimate, sulfohydrolase II has a slightly lower molecular weight of 30.9 kDa when calculated from the amino acid sequence.

From both sequences a theoretical isoelectric point (pI) was calculated using the program Mac Molly translate. Sulfohydrolase I and II are characterized by a pI of 8.4 and 9.3 respectively.

From the amino acid and nucleotide sequences of sulfohydrolase I and II, analogs or homologs of these sulfohydrolases may be detected and isolated using known techniques based upon sequence homology to the sulfohydrolases enzymes disclosed herein. Thus, all or part of the known enzyme coding sequence may be used to construct a probe which will hybridize selectively to identical or highly similar enzyme coding sequences present in genomic or cDNA libraries from a particular source. In particular, nucleotide sequences having a % homology of at least about 25%, more preferably at least about 50%, and most preferably at least about 80%, relative to the specifically identified sequences of the present invention, are in accordance with the present invention. Similarly, amino acid sequences having a % homology of at least 25%, more preferably at least 50%, and most preferably at least 80%, relative to the specifically identified sequences of the present invention, are in accordance with the present invention.

Hybridization techniques include hybridization screening of plated cDNA libraries, and amplification by polymerase chain reaction (PCR) using oligonucleotide primers that correspond to conserved sequence domains. See INNIS et al., *PCR Protocols, a Guide to Methods and Applications*, Academic Press (1990), the disclosure of which is herein incorporated by reference in its entirety.

Further, references regarding the above techniques include AUSUBEL et al., *Current Protocols in Molecular Biology*, Green Publishing Company Assoc. and John Wiley Interscience, (1992); and, BERGER et al., *Guide to Molecular Cloning Techniques*, Academic Press (1987), the disclosures of which are herein incorporated by reference in their entireties.

Homologous sulfohydrolases may be found, for example, by extracting DNA and RNA from the source of interest and conducting Southern hybridization, genomic and cDNA library screening, using a complete or partial sequence from one of the known sulfohydrolases.

For instance, total DNA may be extracted in accordance with the method disclosed in APT et al., "The Gene Family Encoding the Fucoxanthin Chlorophyll Proteins from the Brown Alga *Macrocystis pyrifera*", *Mol. Gen. Genet.*, 246, pp. 455–464 (1995), the disclosure of which is herein incorporated by reference. In this regard, it should be noted that it is often not necessary to remove polysaccharides in the manner described by APT et al.

Southern hybridization may be conducted by, for example, by digesting 7 µg of total DNA of *Chondrus crispus, Eucheuma cottonii, Eucheuma spinosum*, and *Gracilaria gracilis* for 4 hours at 37° C. with 60 U of HindIII, available from Amersham Pharmacia Biotech AB, Uppsala, Sweden, and 80 U of EcoRI, available from Biolabs, Beverly, Mass., USA. After precipitation, the digested DNA may be redissolved in 40 µl of 100 mM Tris (pH 7.5)+10 mM EDTA. The fragments may then be fractionated on a 0.8% agarose gel (migration overnight at 35 V) before being transferred under vacuum for 3 hours on a Hybond-N+membrane, available from Amersham Pharmacia Biotech AB, Uppsala, Sweden, using a "Trans DNA express vacuum blotter" apparatus, available from Appligene, Gaithersburg, Md., USA, under the conditions given by the manufacturer.

Prehybridation and hybridization may be performed at 60° C. for *Chondrus crispus* and at 42° C. for the other algae in the conditions given by SAMBROOK et al., *Molecular Cloning: A Laboratory Manual*, 2nd ed., CSH Laboratory Press, Cold Spring Harbor, N.Y. (1989), the disclosure of which is herein incorporated by reference in its entirety. After hybridization, the membranes were washed as follows:

For all the algae except *Chondrus crispus*

2×SSC+0.1% SDS for 2×20 min; and

1×SSC+0.1% SDS for 2×15 min.

For *Chondrus crispus*

Same as above with an additional wash in 0.5×SSC+0.1%SDS for 15 min.

Southern hybridizations were conducted by using the partial length cDNA encoding for sulfohydrolase I. After digestion of the cDNA with EcoRI and XhoI, both available from Biolabs, Beverly, Mass., 2 fragments were generated: one of 400 bp and the other one of 1600 bp. This latter one was then collected and labelled using the ECF Random-Prime Labelling and detection System, available from Amersham Pharmacia Biotech AB, Uppsala, Sweden. Labelling, hybridization and detection were performed as recommended by the manufacturer.

Southern hybridization may also be done by using the full length cDNA encoding for the sulfohydrolase II. This Southern hybridization reveals one major band of about 2.5 kB as well as 3 other bands (which size is between 4 an 1.2 kB) in *Chondrus crispus*. However, even after 60 hours of exposition, 3 faint visible bands could be detected in *Eucheuma spinosum* and cottonii but nothing could be detected in *Gracilaria gracilis*. Similar results were obtained using the full length cDNA encoding for sulfohydrolase I as a probe.

The results are summarized below:

| Seaweed | sulfohydrolase I cDNA | sulfohydrolase II cDNA |
|---|---|---|
| *Chondrus crispus* | major band + 2–3 faint bands | 1 major band + 3 faint bands |
| *Gigartina skottsbergii* | 1 band + 3–4 faint bands | undetermined |
| *Gracilaria gracilis* | NA | no bands |
| *Eucheuma cottonii* | 1 band + faint bands | 3 faint bands |
| *Eucheuma spinosum* | faint bands | 3 faint bands |

All these results indicate therefore that homologous sulfohydrolases I exist in *E. spinosum, E. cottonii* and in *Gigartina skottsbergii* and homologous sulfohydrolases II exist in *E. spinosum* and in *E. cottonii*, but homology with the respective Chondrus enzymes is low.

Almost pure sulfohydrolase II, which in this case had been purified to 80–90% (w/w) homogeneity, based on the total amount of protein in the sample, was incubated with the iota-precursor giving a gel, whereas the boiled enzyme did not. The enzyme was also incubated in 4 different concentrations with the iota-precursor. Low amounts of enzyme created a soft gel whereas higher amounts gave a stronger gel.

After incubation of nu-carrageenan with sulfohydrolase I, sulfate release was detected but there was no increase in viscosity of the carrageenan sample. In contrast, incubation with sulfohydrolase II resulted in sulfate release and an increase in viscosity. NMR analysis showed that all of the isolated enzyme fractions acted to convert nu-carrageenan to iota-carrageenan.

Because of the observed modifications, the previous theory advanced in U.S. Provisional Application No. 60/133,376 of a sulfohydrolase and an anhydrolase has now been abandoned. This previous theory described the enzymes as possessing two different functions: (1) one enzyme to remove the C-6 sulfate on the nu precursor; and (2) one enzyme to form the 3,6-anhydro-galactose bridge, thereby converting the structure to iota carrageenan. It should be noted, however, that although U.S. Provisional Application No. 60/133,376 apparently failed to accurately describe the mode of action for the enzyme, this provisional application disclosed how to purify and use these enzymes.

While not wishing to be bound by theory, it is now believed that sulfohydrolase I is removing the sulfate groups randomly. In contrast, sulfohydrolase II might act progressively by sliding along the molecule to thereby create stretches of iota, which can aggregate with other similar molecules to create a gel.

When incubating the iota-precursor with first the random enzyme followed by inactivation and thereafter incubation with the processive enzyme, a higher viscosity was obtained when compared to using the processive enzyme alone. It seems that the random enzyme is preparing the polymer in such a way that it is easier for the processive enzyme to slide along the molecule.

Taking into consideration the above, the high purity sulfohydrolases of the present invention allow the tailoring of properties of sulfated compounds.

An advantage of using an enzyme is that it can work at relatively low temperatures, such as 0 to 60° C., more preferably 20 to 55° C., and most preferably 37 to 48° C. Accordingly, the enzyme does not need strong heating to make the carrageenan gel.

The incubation is preferably conducted at a pH of about 5.5 to 9.5, more preferably about 6 to 9.5, and most preferably about 7 to 9. In this regard, incubation with the C. crispus sulfohydrolases is preferably conducted at a pH of about 6.5 to 7.5. Incubation with the Cottonii sulfohydrolase is preferably conducted at a pH of about 8 to 9.5.

The concentration of total proteins of the samples containing the sulfohydrolases is preferably at least about 2 to 85 $\mu$g/ml, more preferably about 10 to 80 $\mu$g/ml, and most preferably about 25 to 70 $\mu$g/ml. In the case of almost pure sulfohydrolase II, the concentration is preferably 1 to 10 $\mu$g/ml, more preferably about 2.5 to 10 $\mu$g/ml, and most preferably about 2.5 to 5 $\mu$g/ml.

The concentration of the substrate, e.g., carrageenan, in the reaction mixture is preferably about 0.012 to 2% (w/v), more preferably about 0.12 to 2% (w/v), and most preferably about 0.7 to 1.75% (w/v).

For incubation with Cottonii extract, the optimal conditions in which the desulfatation reaction should be performed are as follows:

Substrate: mu-carrageenan at a final concentration of about 1.5% (w/v)

Activity /stability as a function of temperature: 9 hours incubation at 48° C. releases as much free sulfate as incubation for 16 hours at 37° C. or 48 hours at 20° C.

Activity/stability as a function of pH: Tris-HCl 100 mM (pH 9.0)+2-mercaptoethanol 10 mM or Bis-tris 100 mM (pH 8.5)+10 mM 2-mercaptoethanol seem to be the most appropriate buffers for the sulfohydrolase of Cottonii Amount of proteins: 5 $\mu$g of total proteins is the minimum amount of material required to get a significant signal on the Dionex.

The purified sulfohydrolases of the present invention are effective in modifying sulfated compounds, e.g., carrageenan. For instance, 1 mg of enzyme extract in accordance with the present invention (in this case 0–30% acetone fraction) is able to release 400 nmoles of sulfate per hour.

Sulfohydrolase I and II may be used separately, or in combination, to modify substrates, and in particular to specifically tailor the number and distribution of sulfate groups and/or anhydro-bridges in carrageenan. The high purity sulfohydrolases of the present invention are especially useful in tailoring properties.

Possibly, the most direct application of this discovery is substitution of enzymatic modification for existing chemical modification processes where comparable (or better) functionality, e.g., gelling properties, viscosity, texture in food, can be achieved with enzymatic modification.

For example, a carrageenan that contains precursor and therefore does not gel, can be induced to gel enzymatically.

As another example, a nu-carrageenan may be converted into an iota-carrageenan to form a product that does not gel under conditions wherein the product has a concentration of about 0.7% (w/v) in an aqueous solution having 0.1 M of potassium at a temperature of 65° C. and a pH of 7.

In addition, and by way of non-limiting example only, the functionality of these enzymes may have the following applications: selective control of the induction of 3,6-anhydrogalactose residues; tailoring those properties of carrageenans which are related to the number and distribution of both the sulfate groups and 3,6-anhydrogalactose residues; inducing modification and gelation of iota-precursor in aqueous systems (including cold gelation of cold-soluble carrageenan solutions and pastes, with representative use including food, pharmaceutical, textile, and personal hygiene products, further including special uses such as dairy products, especially powder formulations, toothpaste, and other paste or slurry products); control of the production of iota carrageenan for gelatin replacement (as the enzyme is expected to give an incomplete modification in comparison with the current alkaline process it will allow better control of the gelatin-like properties which depend on such incomplete modification); modification of only iota-precursor in kappa-iota-precursor mixtures, as for example neutral extracts of cold water seaweed specifies, which may give lower gel strength but increased water-binding capacity as well as other new characteristics; and use with other galactan structures having 6-sulfate groups, including agaroids, as well as with homologous nucleic acids and proteins in carrageenophytes and agarophytes.

The precursor-containing carrageenan may be used by injection into or to coat uncooked meat, e.g., chicken, salmon. If such enzymes are included in the mixture, they will make the carrageenan gel, so that when the meat is cooked, juices are prevented from leaking out of the meat. Further possible uses include the following:

preparation of high molecular weight carrageenan with high viscosity and high gel strength by using mild conditions for extraction of the carrageenan, followed by use of the enzymes for modification of the carrageenan; and gelation at or near ambient temperature (cold gelation), reducing or eliminating the need for heating and/or cooling steps in processes, such as yogurt production, that require the production of a gel.

The present invention will be further illustrated by way of the following Examples. These examples are non-limiting and do not restrict the scope of the invention.

Unless stated otherwise, all percentages, parts, etc. presented in the examples are by weight.

EXAMPLES 1–4

These Examples are directed to studying the specificity of C. crispus sulfohydrolase extracts on different types of carrageenans.

In order to study the specificity of the Chondrus sulfohydrolases, nu-, mu-, iota- and kappa-carrageenans were used as substrates. The iota- and kappa-carrageenans were isolated from their seaweed sources by alkaline extraction giving complete 3,6-anhydrogalactose formation. The precursor-rich carrageenans, containing mu-, nu-, or lambda-carrageenan, were isolated by neutral extraction with water. The lambda-carrageenan was extracted from manually sorted tetrasporophytes. All carrageenans were recovered by precipitation in isopropyl alcohol. These carrageenans, as listed in Table 1 below, were provided by Hercules Incorporated, Lille Skensved, Denmark.

TABLE 1

| Carrageenan | Seaweed Source Botanical Name | Seaweed Trade Name | Sulfate Content (%(w/w)) |
|---|---|---|---|
| Nu | *Eucheuma denticulatum* | Spinosum | 33 |
| Mu | *Kappaphycus alvarezii* | Cottonii | 23 |
| Iota | *Eucheuma denticulatum* | Spinosum | 33 |
| Kappa | *Kappaphycus alvarezii* | Cottonii | 20 |

Before being used, the carrageenans were dialyzed overnight against 10 liters of 50 mM Tris-HCl (pH 7.1) buffer containing 10 mM 2-mercaptoethanol, using a Spectra/por membrane MWCO 6-8000 or 3500, available from Spectrum Laboratories, Inc., Rancho Dominguez, Calif., USA. The final concentration of the carrageenans, after dialysis was about 1.25% (w/v).

Gametophyte plants of *C. crispus* were frozen in liquid nitrogen and ground automatically to pieces which were less than 1 mm long using a Forplex miller, available from Forplex Industrie, Boulogne Billancourt, France. This "powder" was used immediately or kept at −20° C. or −80° C. until further use.

*C. crispus* extracts were prepared in the following manner. Fifteen (15) g of the milled *C. crispus* were extracted with 4 volumes (i.e., 60 ml) of 50 mM Tris-HCl buffer (pH 9.5) containing 10 mM 2-mercaptoethanol and 500 mM KCl. The supernatant was then fractionated with cold (−20° C.) acetone: 2 steps of fractionation were performed: from 0 to 30% saturation and from 30 to 60% saturation of acetone. In this regard, the volume of acetone to add to z ml of sample, when going from A % to B % of cold acetone saturation is determined as follows: $z(B-A)/(100-B)$.

After each fractionation step, a centrifugation was performed at 4° C. for 30 min. at 10,000×g. The pellets were dissolved in 2 ml of 50 mM Tris-HCl buffer (pH 7.1) containing 10 mM 2-mercaptoethanol. The pellets as well as an aliquot of each of the supernatants were then dialyzed overnight at 4° C. against 3×3 liters of 50 mM Tris-HCl buffer (pH 7.1) containing 10 mM 2-mercaptoethanol, using a Spectra/por membrane MWCO 6-8000 or 3500, available from Spectrum Laboratories, Inc., Rancho Dominguez, Calif., USA.

From these extracts, reaction mixtures for screening of activity were made to have the compositions shown in Table 2 below.

TABLE 2

| Component | Control | Sample |
|---|---|---|
| Carrageenan, as listed in Table 3 (1.25% (w/v) in 50 mM Tris-HCl (pH 7.1) + 10 mM 2-mercaptoethanol) | 500 µl | 500 µl |
| 50 mM Tris-HCl (pH 7.1) + 10 mM 2-mercaptoethanol | 500 µl | 250 µl |
| Chondrus extract | 0 µl | 250 µl |

As summarized in Table 3 below, the various carrageenans described above were incubated for 40 hours at room temperature at a pH of 7.1 with the Chondrus extracts obtained in the manner described above. The amount of free sulfate for each Sample was measured using the free sulfate assay method described in the specification. Similarly, the amount of free sulfate was measured by the same assay method for each corresponding Control which included the same carrageenan but which did not include Chondrus extract as shown in Table 2. The difference in free sulfate between each Sample and its corresponding Control is the relative level of sulfate released, as shown in Table 3 below.

TABLE 3

| | | Relative Level of Sulfate Released (ppm) | | | |
|---|---|---|---|---|---|
| Example | Extract | Nu | Mu | Iota | Kappa |
| 1 | supernatant (0–30% acetone) | 101.0 | 15.3 | 6.4 | 6.7 |
| 2 | pellet (0–30% acetone) | 48.1 | 7.1 | 2.4 | 3.2 |
| 3 | supernatant (30–60% acetone) | 72.8 | 16.5 | 4.3 | 6.2 |
| 4 | pellet (30–60% acetone) | 40.6 | 8.7 | 2.6 | 2.0 |

As shown in Table 3, Chondrus extract is active on the nu-carrageenan. The first supernatant (0–30% acetone saturation) and the second supernatant (30–60% supernatant) also display some activity on the mu-carrageenan but the activity on this substrate is relatively low as compared with the activity on the nu-carrageenan.

EXAMPLES 5–38

As shown in the following Examples, in order to determine the optimal conditions for the *C. crispus* sulfohydrolase, a partial characterization of a fractionated *C. crispus* extract was performed which included activity as a function of pH, temperature, enzyme and substrate concentration. From these Examples, it appears that the desulfatation of the nu-carrageenan should be performed for a minimum of 6 to 15 hours at 48° C. using a final substrate concentration of 0.7% (w/v). These Examples also show that Chondrus extract is characterized by a pH optimum around 7, using Tris-HCl (50 mM, pH 7.1+10 mM 2-Mercaptoethanol) as buffer.

Unless otherwise stated, the nu-carrageenan listed in Table 1 was dissolved in Tris-HCl 50 mM (pH 7.1) buffer containing 10 mM 2-mercaptoethanol and dialyzed for 24 hr against 6×2 liters of the buffer, using a Spectra/por membrane MWCO 6-8000 or 3500, available from Spectrum Laboratories, Inc., Rancho Dominguez, Calif., USA, in the same buffer. The substrate was used in the reaction mixture at a final concentration of 0.6% (w/v).

To obtain sulfohydrolase extracts, *C. crispus*, which was powdered in the manner described in Examples 1–4, was fractionated with cold acetone at −20° C. from 0 to 30% or from 30 to 60% of acetone saturation.

The fractions were dialyzed for 16 hours in 4×2.5 liters of 50 mM Tris-HCl (pH 7.1)+10 mM 2-mercaptoethanol buffer. The resulting *C. crispus* extract from 0–30% acetone saturation had a protein concentration of about 170 µg/ml, as measured by using the Bio-Rad protein assay, available from Bio-Rad Laboratories GmbH, Munich, Germany, with bovine serum albumin used as standard.

EXAMPLE 5–13

These Examples are directed to determining the activity of *C. crispus* extract on nu-carrageenan as a function of pH.

In these Examples, 300 mg of the nu-carrageenan were dialyzed for 24 hr against 6×2 liters of MilliQ water, available from Millipore Corporation, Bedford, Mass., USA, using a Spectra/por membrane MWCO 6-8000 or 3500, available from Spectrum Laboratories, Inc., Rancho Dominguez, Calif., USA. The final concentration of carrageenan after dialysis was 1.1% (w/v).

Sample and Control reaction mixtures were prepared as shown in Table 4 below.

TABLE 4

| Component | Control | Sample |
|---|---|---|
| Nu-carrageenan (1.1% (w/v) in water) | 500 μl | 500 μl |
| Buffer (100 mM Tris, Pipes, or Mes, as discussed below) | 250 μl | 250 μl |
| 50 mM Tris-HCl pH 7.1 | 250 μl | 0 μl |
| Chondrus extract (in 50 mM Tris-HCl pH 7.1) (0 to 30% acetone saturation) | 0 μl | 250 μl |

Depending upon the pH required, as shown in Table 5 below, the buffers used in the reaction mixtures were the following:

pH 5.5 to 6.5: 100 mM MES (2-(N-morpholino) ethanesulfonic acid)+10 mM 2-mercaptoethanol;

pH 6.5 and 7.0: 100 mM Pipes (piperazine-N,N' (2-ethanesulfonic acid)+10 mM 2-mercaptoethanol; and pH 7.0 to 9.0: 100 mM Tris-HCl+10 mM 2-mercaptoethanol.

The pH of the buffer was varied by adding HCl in the case of Tris-HCl or by adding NaOH in the cases of MES and Pipes.

The reaction mixtures were incubated for 26 hr at 29° C. After incubation, the amount of sulfate released was measured in accordance with the free sulfate assay method described in the specification. By comparing the amount of free sulfate in the Samples and their corresponding Controls, the relative amount of free sulfate, shown in Table 5 below, was calculated.

TABLE 5

| | | Relative Level of Sulfate Released (ppm) | | | % Relative |
|---|---|---|---|---|---|
| Example | pH | MES | Pipes | Tris-HCl | Activity |
| 5 | 5.5 | 2.7 | | | 6.6 |
| 6 | 6 | 20.0 | | | 48.7 |
| 7 | 6.5 | 31.2 | | | 75.9 |
| 8 | 6.5 | | 29.8 | | 72.5 |
| 9 | 7 | | 32.6 | | 79.3 |
| 10 | 7 | | | 41.1 | 100 |
| 11 | 8 | | | 32.1 | 78.1 |

TABLE 5-continued

| | | Relative Level of Sulfate Released (ppm) | | | % Relative |
|---|---|---|---|---|---|
| Example | pH | MES | Pipes | Tris-HCl | Activity |
| 12 | 8.5 | | | 23.0 | 56.0 |
| 13 | 9 | | | 23.5 | 57.2 |

Table 5 shows that the pH optimum of the *C. crispus* extract was about 7.

EXAMPLES 14–21

These examples are directed to determining the activity of *C. crispus* extract on nu-carrageenan as a function of quantity of protein, including sulfohydrolase, in the extract.

Sample and Control reaction mixtures were prepared in the proportions shown in Table 6 below.

TABLE 6

| Ex. | Nu-carrageenan (1.25% (w/v) in 50 mM Tris-HCl (pH 7.1) + 10 mM 2-mercaptoethanol) | Chondrus extract (170 μg/ml of protein)(0 to 30% acetone saturation) | 50 mM Tris-HCl (pH 7.1) + 10 mM 2-mercaptoethanol |
|---|---|---|---|
| Control | 500 μl | 0 μl | 500 μl |
| 14 | 500 μl | 50 μl | 450 μl |
| 15 | 500 μl | 100 μl | 400 μl |
| 16 | 500 μl | 150 μl | 350 μl |
| 17 | 500 μl | 200 μl | 300 μl |
| 18 | 500 μl | 250 μl | 250 μl |
| 19 | 500 μl | 300 μl | 200 μl |
| 20 | 500 μl | 400 μl | 100 μl |
| 21 | 500 μl | 500 μl | 0 μl |

The above Control and Sample mixtures having different concentrations of sulfohydrolase extract were incubated for 30 hr at 30° C. at a pH of 7.1. After incubation, the amount of sulfate released was measured in accordance with the free sulfate assay method described in the specification. By comparing the amount of free sulfate in the Samples and their corresponding Controls, the relative amount of free sulfate, shown in Table 7 below, was calculated.

TABLE 7

| Example | Amount of protein (μg) | Relative Level of Sulfate Released in 30 hours (ppm) |
|---|---|---|
| 14 | 8.5 | 14.1 |
| 15 | 17 | 24.5 |
| 16 | 25.5 | 34.2 |
| 17 | 34 | 40.2 |
| 18 | 42.5 | 54.6 |
| 19 | 51 | 53.1 |
| 20 | 68 | 74.7 |
| 21 | 85 | 65.2 |

Table 7 shows, as expected, that increasing the amount of enzyme preparation increases the amount of sulfate released.

EXAMPLES 22–32

These examples are directed to determining the activity of *C. crispus* extract as a function of nu-carrageenan concentration.

Control and Sample reaction mixtures were made in the same manner as described in Table 1 above, except that the volume of the reaction mixtures was reduced to 500 μl, i.e., the volume of all components was reduced by 50%, and except that the 30–60% acetone saturation Chondrus extract was used.

In order to determine the optimal concentration of nu carrageenan to use during the desulfatation reaction, 12 different concentrations of nu carrageenan, ranging from 0 to 2.5% (w/v) (final concentrations) were tested, as shown in Table 8 below.

After incubation for 15 hours at 37° C., the amount of sulfate released was measured in accordance with the free sulfate assay method described in the specification. By comparing the amount of free sulfate in the Samples and their corresponding Controls, the relative amount of free sulfate, shown in Table 8 below, was calculated.

TABLE 8

| Ex. | Nu-carrageenan in reaction mixture (final % (w/v)) | Relative Level of Sulfate Released (ppm) | % relative activity |
| --- | --- | --- | --- |
| 22 | 0.37 | 40.0 | 81.3 |
| 23 | 0.54 | 47.3 | 96.0 |
| 24 | 0.7 | 49.2 | 100 |
| 25 | 0.85 | 43.8 | 88.9 |
| 26 | 1.03 | 44.6 | 90.5 |
| 27 | 1.12 | 43.0 | 87.3 |
| 28 | 1.27 | 19.0 | 38.6 |
| 29 | 1.45 | 9.0 | 18.3 |
| 30 | 1.76 | 39.8 | 80.8 |
| 31 | 2.07 | 29.1 | 59.1 |
| 32 | 2.49 | 33.1 | 67.2 |

Table 8 shows that 0.7% (w/v) of nu-carrageenan (final concentration in the reaction mixture) is the optimal concentration of substrate to use for the desulfatation reaction by the nu sulfohydrolase.

EXAMPLES 33–38

These examples are directed to determining the activity of *C. crispus* extract on nu-carrageenan as a function of temperature.

Control and Sample reaction mixtures were made in the same manner as described in Examples 1–4 above, except that the 30–60% acetone saturation Chondrus extract was used.

Reaction mixtures were incubated at 0, 13, 20, 30, 37 and 48° C. at a pH of 7.1. In order to measure the amount of free sulfate released as a function of time, small aliquots (about 0.2 ml) of reaction mixture were taken after 0, 2, 8, 26, 46 and 72 hr of incubation at the above mentioned temperatures.

TABLE 9

| | | Relative Level of Sulfate Released (ppm) | | | | | |
| --- | --- | --- | --- | --- | --- | --- | --- |
| Ex. | Temperature (° C.) | 0 hours | 2 hours | 8 hours | 26 hours | 46 hours | 72 hours |
| 33 | 0 | 0.2 | 1.8 | 2.0 | 0 | 7.2 | 11.6 |
| 34 | 13 | 0 | 2.7 | 9.0 | 15.2 | 29.2 | 27.0 |
| 35 | 20 | 0.2 | 4.9 | 13.6 | 26.1 | 44.7 | 47.5 |
| 36 | 30 | 0.25 | 7.1 | 13.2 | 39.7 | 61.8 | 51.6 |
| 37 | 37 | 0.3 | 9.0 | 22.9 | 44.6 | 77.8 | 58.6 |
| 38 | 48 | 0.3 | 14.6 | 34.8 | — | — | — |

Table 9 shows that the amount of sulfate released from the nu-carrageenan increases with the temperature. In particular, 48° C. seems to be the optimal temperature for the crude extract. In fact, an incubation of 8 hours at 48° C. releases as much free sulfate as a 40 hour incubation at room temperature.

EXAMPLES 39–46

These examples are directed to studying the specificity of pure, based on total protein content, *C. crispus* sulfohydrolase II on different types of carrageenans.

Pure, based on total protein content, *C. crispus* sulfohydrolase II was isolated by using the protocol described in the specification. In particular, the fractions of pure *C. crispus* sulfohydrolase II elute from the DEAE chromatography column with a concentration of NaCl between 650 and 850 mM.

The specificity of the pure sulfohydrolase II was tested on different types of carrageenans. In particular, Control and Sample reaction mixtures as shown in Table 10 below, were made by using the carrageenans shown in Table 11. Thus, the pure sulfohydrolase II was tested on a nu enriched iota-carrageenan (shown as preparation method "E" in Table 11). The pure sulfohydrolase II was also tested on enzyme resistant fractions of nu enriched iota- and iota-carrageenan incubated with iotase, as described below (shown as preparation method "ER" in Table 11). The pure sulfohydrolase II was further tested on neutral extracted iota- and kappa-carrageenan, which was prepared as described below (shown as preparation method "N" in Table 11). Still further, the pure sulfohydrolase II was tested on the nu enriched iota- and mu enriched kappa-carrageenan which were made as described below (shown as preparation method "C" in Table 11).

The preparation method "E" of Table 11 for preparing nu enriched iota-carrageenan was as follows. Fifteen (15) kg of *Eucheuma denticulatum* was washed 3 times in 80% (w/v) of isopropyl alcohol, dried in a drying chamber at 60° C. until constant weight and milled to 0.5 mm particle diameter. The milled seaweed was extracted at 50° C. for 4 hours in 1000 liter of 0.125 M KCl/$K_2CO_3$ (9.15 kg KCl and 0.17 kg). During the extraction, the pH was measured to ensure that it was between 8 and 9. If the pH was lower than 8, an appropriate amount of $K_2CO_3$ was added.

The extract liquid was filtered on kiselgur-filter, and the extract juice was washed in UF (ultrafiltration) with tap water until the conductivity was at 2 mS/cm (<2000 μS/cm) or lower and stable. Then, the juice was concentrated to about 65–70 liter total. The pH was adjusted with 0.1 M NaOH to approximately 8.5. In this regard, 1–10 deciliter of the 0.1 M NaOH was added with a pipette while stirring and closely monitoring the pH. A precipitation test was conducted in 100% (w/v) isopropyl alcohol—and if precipitate is formed, all is precipitated. If precipitation is poor, the juice was concentrated by evaporation under vacuum and pH and temperature are closely followed. The juice must not exceed 9.2 in pH. In some cases, it was necessary to let the carrageenan precipitate overnight. The precipitated carrageenan was washed a couple of times in 100% (w/v) isopropyl alcohol. All steps were conducted at room temperature. The carrageenan was freeze-dried. NMR results indicated that the precursor level was enriched to about 32% of total weight.

The iota-carrageenan was prepared in the same manner as the iota-carrageenan shown of Table 1 above.

The preparation of enzyme resistant fractions (method "ER" of Table 11) of the nu enriched iota- and iota-carrageenans was carried out as follows. The starting material was either the nu enriched iota-carrageenan was obtained via method "E" described above, or the iota-carrageenan listed in Table 1.

With either of these starting materials, one gram of the carrageenan to be made enzyme resistant was dissolved in 50 mM tris-HCl (pH 7.0)+100 mM NaCl and 5 mM $CaCl_2$. The resulting digestion mixture was incubated for 4 hours at 37° C. by additions of 0.2 U of iota carrageenase, which had been purified in accordance with POTIN et al., "Purification and Characterization of a New κ-Carrageenase from a Marine Cytophaga-like Bacterium", *Eur. J. Biochem.*, 201, pp. 241–247 (1991), the disclosure of which is herein incorporated by reference in its entirety, per mg of carrageenan with 2 hours intervals. One unit of enzyme activity (U) is defined as the amount of enzyme which produces an increase of 0.1 absorbance unit at 237 nm per minute in the reducing sugar assay in accordance with KIDBY et al., "A Convenient Ferricyanide Estimation of Reducing Sugars in the Nanomole Range", *Analytical Biochemistry*, 55, pp. 321–325 (1973), the disclosure of which is herein incorporated by reference in its entirety. The first enzyme resistant fraction (ERF1) was obtained after precipitation with 2 volumes of ethanol 50% (v/v). After centrifugation for 20 min at 10,000×g and 4° C., the pellet was collected and considered as ERFI. Two (2) volumes of 95% (v/v) ethanol were then added to the supernatant. After centrifugation under the same conditions as before, the pellet was collected and named ERF2. ERF1 and ERF2 were separately redissolved in water and dialyzed 5×2 liters of 20 mM $(NH_4)HCO_3$, using a Spectra/por membrane MWCO 6-8000 or 3500, available from Spectrum Laboratories, Inc., Rancho Dominguez, Calif., USA. The ERF1 and ERF2 were then freeze-dried.

The neutral extraction method (i.e., method "N" of Table 11 below) was as follows. Extraction of 200 g of seaweed, as listed in Table 11, was conducted in 10 liters of tap water for 35 minutes at 1 10° C., followed by filtration, concentration, and precipitation in isopropyl alcohol, as described in THERKELSEN, "Carrageenan", *Industrial Gums: Polysaccharides and their Derivatives*, 3rd ed., pp. 145–180, (1993), the disclosure of which is herein incorporated by reference in its entirety.

The preparation method "C" was in accordance with preparation method "E", described above, except that the starting material was Cottonii (=*Kappaphycus alvarezii*).

Referring to Table 11, the reaction mixtures were incubated for 14 hours at a pH of 7.1 at 48° C. The amount of sulfate released was measured in accordance with the free sulfate assay method described in the specification. By comparing the amount of free sulfate in the Samples and their corresponding Controls, the relative amount of free sulfate, shown in Table 11 below, was calculated.

TABLE 10

| Component | Control | Sample |
| --- | --- | --- |
| Carrageenan, as listed in Table 5 (1.4% (w/v) in MilliQ water) | 200 μl | 200 μl |
| Pure sulfohydrolase II boiled for 10 minutes | 200 μl | 0 μl |
| Pure sulfohydrolase II | 0 μl | 200 μl |

TABLE 11

| Ex. | Carrageenan | Preparation Method | Carrageenan Source | Relative Level of Sulfate Released (ppm) |
| --- | --- | --- | --- | --- |
| 39 | Nu enriched iota | E | *E. spinosum* | 87.7 |
| 40 | ERF1 | ER | *E. spinosum* | 4.9 |
| 41 | ERF2 | ER | *E. spinosum* | 77.3 |
| 42 | Neutral extracted iota | N | *E. spinosum* | 43.8 |
| 43 | Nu enriched iota | C | *G. skottsbergii* | 9.0 |
| 44 | Neutral extracted iota | N | *G. skottsbergii* | 7.4 |
| 45 | Mu enriched kappa | C | *K. alvarezii* | 1.4 |
| 46 | Neutral extracted kappa | N | *K. alvarezii* | 1.6 |

Table 11 shows, as expected from the screening study, that the *C. crispus* sulfohydrolase II is not active on kappa-carrageenan or on its precursor, i.e., mu-carrageenan. The *C. crispus* sulfohydrolase II is only active on the neutral extracted iota-carrageenan from Spinosum or its nu-enriched counterparts. Surprisingly, ERF1 of this nu-carrageenan is not a good substrate for sulfohydrolase II. While not wishing to be bound by theory, the ERF1 is believed to contain relatively high molecular weight nu-carrageenan. In contrast, sulfohydrolase II is active on ERF2. While not wishing to be bound by theory, the ERF2 is believed to contain relatively medium or small molecular weight nu-carrageenan. The observed activity on ERF2 and the observed inactivity on ERF1 is not completely understood.

EXAMPLE 47–53

These examples are directed to studying the influence of temperature on the activity/stability of pure, based on protein content, *C. crispus* sulfohydrolase II on different types of carrageenans.

Pure, based on protein content, *C. crispus* sulfohydrolase II was isolated by using the protocol described in the specification. In particular, fractions 59 to 61 from DEAE sepharose chromatography were pooled and used as the source of the sulfohydrolase II.

One volume of the pool of fractions 59 to 61 from the DEAE sepharose chromatography was incubated with one volume of nu-carrageenan, made in accordance with the procedures of Examples 5–12, 1.4% (w/v) in 50 mM tris-HCl+10 mM 2-mercaptoethanol (pH 7.1). Reference mixtures were prepared the same way except that the enzyme (pure sulfohydrolase II) was boiled for 10 minutes under atmospheric pressure prior to incubation with the nu-carrageenan.

As shown in Table 12, reaction mixtures as well as reference mixtures were incubated at different temperatures, from 0° C. to 60° C. Aliquots were taken after 3, 8, 15, 24, 32, and 40 hours of incubation at the above-mentioned temperatures. Results are expressed as the relative amount of sulfate released, measured by using the assay described in the specification, as a function of the period of incubation.

TABLE 12

| Ex. | Temp. (° C.) | Relative Level of Sulfate Release at Time (hours) | | | | |
|---|---|---|---|---|---|---|
| | | 3 | 8 | 15 | 24 | 32 | 40 |
| 47 | 0 | 0 | 0 | 1.7 | 2.1 | 3.9 | 3.2 |
| 48 | 12 | 0 | 0 | 6.0 | 6.1 | 10.3 | 12.9 |
| 49 | 20 | 2.4 | 4.7 | 13.6 | 14.0 | 25.3 | 30.5 |
| 50 | 30 | 4.7 | — | 21.4 | 29.0 | 32.3 | 27.0 |
| 51 | 37 | 9.0 | 15.7 | 34.3 | 41.2 | 53.5 | 35.4 |
| 52 | 48 | — | 26.6 | 55.7 | 73.0 | 97.2 | 97.7 |
| 53 | 60 | 15.2 | 16.3 | 14.6 | 33.3 | 35.3 | — |

As seen from Table 12, the sulfohydrolase appears to have maximum activity around 48° C. Above that temperature, there is a loss of activity due to the denaturation of the enzyme.

EXAMPLES 54–95

These Examples are directed to characterizing the sulfohydrolase activity of extracts from *Kappaphycus alvarezii* (Cottonii).

Cottonii was provided alive by Genu Philippines, Cebu, Philippines. The Cottonii was frozen in liquid nitrogen upon arrival and kept at −80° C. until further use. Prior to extraction the *Cottonii* was ground manually to a fine powder in a mortar, using liquid nitrogen which was poured with a baker into the mortar to keep the *Cottonii* frozen during the grinding.

EXAMPLES 54–57

These Examples are directed to treating various carrageenans with various Cottonii sulfohydrolase extracts to screen for activity. Extracts of Cottonii were prepared as described in Examples 1–4 for *C. crispus*. In this case, however, an additional step of fractionation was performed as the supeernatant was also brought from 60 to 85% saturation in cold acetone. The amount of acetone to add was calculated as described in Examples 1–4. After each step of fractionation, centrifugation was performed as described in Examples 1–4. The pellets were then redissolved in 50 mM Tris-HCl (pH 7.1)+10 mM 2-mercaptoethanol, before being dialyzed overnight at 4° C. against 3×3 liters of the above mentioned buffer. The volume of samples after dialysis was about 1.5 ml.

Control and Sample reaction mixtures were made in accordance with Examples 1–4, except that the extract was from *Cottonii* as opposed to *C. crispus*. Thus, as shown in Table 13 below, in some cases, raw extract from Cottonii was fractionated with acetone.

As shown in Table 13, incubation of the carrageenan was performed for 40 hr at 25 ° C. with various extracts. The amount of released sulfate was measured using the assay method described in the specification.

TABLE 13

| | Cottonii | Sulfate released in various substrates (ppm) | | | |
|---|---|---|---|---|---|
| Example | Extract | Nu | Mu | Iota | Kappa |
| 54 | Raw | 0 | 18.9 | 3.5 | 7.2 |
| 55 | 0–30% acetone (pellet) | 0 | 85.9 | 2.2 | 24.1 |
| 56 | 30–60% acetone (pellet) | 58.9 | 37.1 | 0 | 1.6 |
| 57 | 60–85% acetone (pellet) | 0 | 1 | 0 | 17 |

As shown in Table 13, even when it is not fractionated, the extract of Cottonii is active toward the mu-carrageenan. The same extract, fractionated from 0 to 30% or from 30 to 60% acetone shows a higher activity toward the same substrate. One of the extracts also shows activity toward nu-carrageenan.

EXAMPLES 58–75

These examples are directed to determining the activity of the Cottonii sulfohydrolase as a function of mu-carrageenan concentration.

A 30–60% acetone fraction (pellet) of Cottonii extract was dialyzed overnight at 4° C. against 3×3 liters of 50 mM Tris-HCl (pH 7.1)+10 mM 2-mercaptoethanol by using a MWCO 6-8000 or 3500 dialysis membrane available from Spectrum Laboratories, Inc., Rancho Dominguez, Calif., USA.

Control and Sample reaction mixtures having the components listed in Table 14 were prepared. To prepare these reaction mixtures, two stock solutions were prepared. Stock 1 was 1.25% (w/v) of mu-carrageenan and Stock 2 was 5% (w/v) mu-carrageenan, both in 50 mM tris-HCl (pH 7.1)+10 mM 2-mercaptoethanol. In Table 14, the buffer is 50 mM tris-HCl (pH 7.1)+10 mM 2-mercaptoethanol. The concentration of protein in the extracts was estimated to be about 105 μg/ml, using the Bio-Rad protein assay, available from Bio-Rad Laboratories GmbH, Munich, Germany, with bovine serum albumin used as standard.

TABLE 14

| Ex. | Extract (μl) | Stock 1 (μl) | Stock 2 (μl) | Buffer (μl) | Final Concentration of Mu (% (w/v)) |
|---|---|---|---|---|---|
| Control | 125 | 0 | 0 | 375 | 0 |
| 58 | 125 | 5 | 0 | 370 | 0.012 |
| 59 | 125 | 10 | 0 | 365 | 0.025 |
| 60 | 125 | 20 | 0 | 355 | 0.05 |
| 61 | 125 | 50 | 0 | 325 | 0.125 |
| 62 | 125 | 75 | 0 | 300 | 0.187 |
| 63 | 125 | 100 | 0 | 275 | 0.25 |
| 64 | 125 | 150 | 0 | 225 | 0.375 |
| 65 | 125 | 200 | 0 | 175 | 0.5 |
| 66 | 125 | 250 | 0 | 125 | 0.625 |
| 67 | 250 | 0 | 74 | 676 | 0.37 |
| 68 | 250 | 0 | 110 | 640 | 0.55 |
| 69 | 250 | 0 | 140 | 610 | 0.7 |
| 70 | 205 | 0 | 170 | 580 | 0.85 |
| 71 | 250 | 0 | 200 | 550 | 1 |
| 72 | 250 | 0 | 220 | 530 | 1.1 |
| 73 | 250 | 0 | 300 | 450 | 1.5 |
| 74 | 250 | 0 | 350 | 400 | 1.75 |
| 75 | 250 | 0 | 400 | 350 | 2 |

The Control and Sample reaction mixtures were incubated for 40 hours at 25° C. at of 7.1 with different concentrations of mu-carrageenan as shown in Table 15, below. of sulfate released was measured in accordance with the free sulfate assay method described The relative amount of sulfate released was measured using the assay method described in the specification.

TABLE 15

| Example | Final Concentration of Mu (% (w/v)) | Relative Level of Sulfate Released (ppm) |
|---|---|---|
| 58 | 0.012 | 3.8 |
| 59 | 0.025 | 5.1 |
| 60 | 0.05 | 5.8 |

TABLE 15-continued

| Example | Final Concentration of Mu (% (w/v)) | Relative Level of Sulfate Released (ppm) |
|---|---|---|
| 61 | 0.125 | 11.9 |
| 62 | 0.187 | 17.9 |
| 63 | 0.25 | 19.7 |
| 64 | 0.37 | 22.2 |
| 65 | 0.375 | 23.2 |
| 66 | 0.5 | 31.2 |
| 67 | 0.5 | 26.7 |
| 68 | 0.625 | 32.8 |
| 69 | 0.7 | 32.6 |
| 70 | 0.85 | 36.9 |
| 71 | 1 | 29.2 |
| 72 | 1.1 | 29.6 |
| 73 | 1.5 | 66.1 |
| 74 | 1.75 | 65.4 |
| 75 | 2 | 55.9 |

As seen from Table 15, around 1.75% (w/v) mu-carrageenan was the optimal concentration of substrate to use for the desulfatation reaction by the Cottonii extract. In fact at this concentration, the amount of sulfate released was about twice as much as the amount of sulfate released for mu-carrageenan concentrations of 0.5 to 1% (w/v).

EXAMPLES 76–81

These Examples are directed to determining the activity of the Cottonii sulfohydrolase on mu-carrageenan as a function of temperature.

A 0–30% acetone fraction (pellet) of Cottonii extract was dialyzed overnight at 4° C. against 3×3 liters of 50 mM Tris-HCl (pH 7.1)+10 mM 2-mercaptoethanol by using a MWCO 6-8000 or 3500 dialysis membrane available from Spectrum Laboratories, Inc., Rancho Dominguez, Calif., USA.

Control and Sample reaction mixtures were made in the same manner as Examples 54–57. Thus, the amount of the Cottonii extract was 250 μl. Additionally, the amount of mu-carrageenan solution (1.25% (w/v) in 50 mM Tris-HCl (pH 7.1)+10 mM 2-mercaptoethanol) in the Sample reaction mixtures was 500 μl.

The incubations were conducted at a pH of 7.1 at the different temperatures listed in Table 16, below. Aliquots of the reaction mixture were removed at the different times listed in Table 16, below, and the relative amount of sulfate released was measured by using the method described in the specification.

TABLE 16

| | | Relative Amount of Sulfate Released (ppm) | | | | |
|---|---|---|---|---|---|---|
| Example | Temperature (° C.) | 3 hours | 9 hours | 27 hours | 48 hours | 70 hours |
| 76 | 4 | 2.4 | 2.6 | 25.5 | 15.9 | 42.1 |
| 77 | 12 | 10.2 | 6.4 | 29.5 | 38.8 | 79.4 |
| 78 | 20 | 11 | 18.4 | 53.5 | 59.4 | 79.8 |
| 79 | 30 | 17.8 | 34.8 | — | 61.7 | 90.4 |
| 80 | 37 | 24 | 49.7 | 74.4 | 73.2 | 90.4 |
| 81 | 48 | 11.9 | 61.8 | 81.2 | 77.2 | 105 |

Table 16 shows that although the extract is active at low temperature (4° C.), the mu sulfohydrolase extract from Cottonii displayed a maximum of activity at 48° C. In this regard, it should be noted that 48° C. was the maximum temperature tested such that the extract may have higher activity at even higher temperatures. In any case, at 48° C., significant sulfate was released after 9 hours of incubation of the enzyme with the mu-carrageenan.

EXAMPLES 82–95

These examples are directed to determining the activity of the Cottonii sulfohydrolase on mu-carrageenan as a function of pH.

The Cottonii extract used in these Examples was estimated to have a concentration of proteins of about 105 μg/ml, using the Bio-Rad protein assay, available from Bio-Rad Laboratories GmbH, Munich, Germany, with bovine serum albumin used as standard. Sample and Control reaction mixtures were prepared as shown in Table 17 below.

TABLE 17

| Component | Control | Sample |
|---|---|---|
| Mu-carrageenan (1.2% (w/v) in water) | 250 μl | 250 μl |
| Buffer (100 mM Tris, Pipes, Mes, or Bis-Tris, as discussed below) | 125 μl | 125 μl |
| 50 mM Tris-HCl pH 7.1 + 10 mM 2-mercaptoethanol | 125 μl | 0 μl |
| Cottonii extract (in 50 mM Tris-HCl pH 7.1 + 10 mM 2-mercaptoethanol) | 0 μl | 125 μl |

In these Examples, the pH was varied generally in accordance with the method of Examples 5–13 which are directed determining the activity of the *C. crispus* sulfohydrolase. In addition to the buffers described for *C. crispus*, in order to determine the pH optimum, bis-tris buffer (100 mM bis tris +2-mercaptoethanol 10 mM) was used (from pH 8.0 to 9.5). The bis-tris being (bis[2-Hydroxyethyl]iminotris [hydroxymethyl]methane; 2-bis[2-Hydroxyethyl]amino-2-[hydroxymethyl]-1,3-propanediol), available from Sigma Chemical, St. Louis, Mo., USA.

The reaction mixtures were incubated for 18 hr at 48° C. After incubation, the amount of sulfate released was measured in accordance with the free sulfate assay method described in the specification. By comparing the amount of free sulfate in the Samples and the Control, the relative amount of free sulfate, shown in Table 18 below, was calculated.

TABLE 18

| | | Sulfate Released (ppm) | | | |
|---|---|---|---|---|---|
| Example | pH | MES | Pipes | Tris-HCl | Bis-Tris |
| 82 | 5.5 | 1.94 | | | |
| 83 | 6 | 19.8 | | | |
| 84 | 6.5 | 49.8 | | | |
| 85 | 6.5 | | 58.0 | | |
| 86 | 7 | | 58.1 | | |
| 87 | 7 | | | 47.4 | |
| 88 | 7.5 | | | 54.4 | |
| 89 | 8.2 | | | 56.5 | |
| 90 | 8.2 | | | | 73.2 |
| 91 | 8.5 | | | 69.0 | |
| 92 | 8.5 | | | | 71.6 |
| 93 | 9 | | | 85.6 | |
| 94 | 9 | | | | 18.8 |
| 95 | 9.5 | | | | 41.0 |

Table 18 shows that the pH optimum of the mu-sulfohydrolase is between 8.2 and 9.0, depending on the buffer used in the reaction mixture. Thus, the optimal pH for the Cottonii extract is more alkaline than the optimal pH for *Chondrus crispus* extract.

EXAMPLES 96–104 AND COMPARATIVE EXAMPLE 1

These Examples and Comparative Example are directed to determining the activity of the Cottonii sulfohydrolase on mu-carrageenan as a function of quantity of proteins.

The concentration of proteins in the Cottonii extract was estimated to be 105 µg/ml for the Examples and Comparative Example. Reaction mixtures in which the amount of protein was varied were made in accordance with Table 19 below. The reaction mixtures were incubated for 18 hours at 48° C. at a pH of 7.1.

In Table 19, the buffer was 50 mM Tris-HCl pH 7.1+10 mM 2-mercaptoethanol. The amount of sulfate released, as measured in accordance with the method described in the specification, is shown in Table 19 below.

TABLE 19

| Example | Cottonii Extract (µl) | Buffer (µl) | 1.2% (w/v) Mu-carrageenan in water (µl) | Quantity of Protein (µg) | Sulfate Released (ppm) |
| --- | --- | --- | --- | --- | --- |
| Comp. 1 | 0 | 250 | 250 | 0 | 1.9 |
| 96 | 5 | 245 | 250 | 0.52 | 5.7 |
| 97 | 10 | 240 | 250 | 1.05 | 7.2 |
| 98 | 20 | 230 | 250 | 2.10 | 10.4 |
| 99 | 50 | 200 | 250 | 5.20 | 17.9 |
| 100 | 75 | 175 | 250 | 7.90 | 26.2 |
| 101 | 100 | 150 | 250 | 10.50 | 30.8 |
| 102 | 150 | 100 | 250 | 15.70 | 50.2 |
| 103 | 200 | 50 | 250 | 21.00 | 66.8 |
| 104 | 250 | 0 | 250 | 26.20 | 84.5 |

Table 19 shows that the mu sulfohydrolase is an active enzyme since as little as 5 µg of total proteins was enough to release a significant amount of sulfate.

EXAMPLE 105

This Example is directed to isolation and partial purification of the mu-sulfohydrolase enzyme from Cottonii.

Fifty (50) g of fresh Cottonii provided by Genu Philippines, Cebu, Philippines were frozen in liquid nitrogen and ground using a Grinomix GM 200 miller, available from Retsch BV, Germany. The powder was then allowed to thaw for about 60 hours at 4° C. in 1.5 volumes, i.e., 75 ml, of 50 mM Tris-HCl (pH 9.5)+10 mM 2-mercaptoethanol+500 nM KCl. The extract was centrifuged at 4° C. at 24,000×g for 90 minutes.

The supernatant was then tested for sulfohydrolase activity with 1.5% (w/v) nu- or mu-carrageenan in 50 mM Tris-HCl pH 7.1+10 mM 2-mercaptoethanol. Incubation with the Cottonii extract was performed for 20 hours at 48° C. The incubation mixture contained 250 µl 50 mM Tris-HCl+10 mM 2-mercaptoethanol at pH 7.1, 500 µl of extract, and 500 µl of substrate (1.5% (w/v) in Tris-HCl (50 mM)+10 mM 2-mercaptoethanol at pH 7.1. The amount of sulfate released was measured as described in the specification.

Sulfate release was highest with the iota-precursor (80 ppm after 20 hours) and lowest for the kappa-precursor (10–30 ppm after 20 hours). In particular, 11 ppm of free sulfate were released when the substrate was the mu-carrageenan described in Table 1, whereas 29 ppm of free sulfate were released when the substrate was the mu-carrageenan made in accordance with the "C" method described in Examples 39–46.

To further purify the sulfohydrolase, the extract was brought to 30% saturation of ammonium sulfate by adding 16.4 g of ammonium sulfate/100 ml of sample. After 16 hours at 4° C., the sample was then centrifuged at 24,000×g for 90 minutes at 4° C. The supernatant (40 ml) was loaded at a flow rate of 3 ml/min on a Phenyl Sepharose 6 fast flow (high sub) column, available from Amersham Pharmacia Biotech AB, Uppsala, Sweden, previously equilibrated in 50 mM Tris-HCl (pH 8.7)+10 mM 2-mercaptoethanol+500 mM KCl+30% of saturation of ammonium sulfate. The column was washed with this buffer until the absorbance at 280 nm was negligible. Then, the proteins were eluted using a decreasing gradient in ammonium sulfate, as described below and in Table 20:

Buffer A: 50 mM Tris-HCl (pH 8.7)+10 mM 2-mercaptoethanol+500 mM KCl+30% of saturation of ammonium sulfate Buffer B: 50 mM Tris-HCl (pH 8.7)+10 mM 2-mercaptoethanol+500 mM KCl Fraction Size: 5 ml Flow Rate: 3 ml/min

TABLE 20

| Time (min) | % of Buffer A | % of Buffer B |
| --- | --- | --- |
| 0 | 100 | 0 |
| 120 | 0 | 100 |

EXAMPLES 106–109 AND COMPARATIVE EXAMPLE 2

These Examples are directed to purification of sulfohydrolase I and II from *C. crispus*.

Both sulfohydrolase I and II from *Chondrus crispus* were purified to homogeneity. The extraction of the enzymes was started with two batches of 0.6–0.7 kg of fresh seaweed, followed by two runs on a Phenyl Sepharose column. Active fractions (in terms of sulfate released) were pooled, dialyzed for 36 hours against 5×10 liters of 50 mM Tris-HCl buffer (pH 7.1) containing 10 mM 2-mercaptoethanol (buffer A), using a Spectra/por membrane MWCO 6-8000 or 3500, available from Spectrum Laboratories, Inc., Rancho Dominguez, Calif., USA. The dialyzed fractions were then loaded on to a DEAE Sepharose column, available from Amersham Pharmacia Biotech AB, Uppsala, Sweden, giving the pure sulfohydrolase II. Half of one fraction, which contains sulfohydrolase I as well as many other proteins, was loaded to a HiTrap heparin column, available from Amersham Pharmacia Biotech AB, Uppsala, Sweden, giving the pure sulfohydrolase I.

The concentration of the pure sulfohydrolase I and II in the fractions was very low and could not be determined using Bio-Rad Protein assay available from Bio-Rad Laboratories GmbH, Munich, Germany, with bovine serum albumin used as standard, as the amount of pure sulfohydrolase I and II present in solution is below the detection limit.

Reactions mixtures as shown in Table 21 below were incubated for 14 hours at 48° C. In these reaction mixtures, different amounts of almost pure (about 80% (w/w) based on the total amount of proteins) sulfohydrolase II having a concentration estimated to be 30 µg/ml using the Bio-Rad Protein assay, available from Bio-Rad Laboratories, Munich, Germany, was incubated with iota-precursor, obtained in accordance with method "E" described above in Examples 39–46, giving a gel. In contrast, when the enzyme was boiled at 100° C. for 10 minutes prior to incubation, incubation under the same conditions did not result in a gel.

After incubation, all the reaction mixtures were boiled for 10 minutes at 100° C. in order to stop the reaction.

Comparative Example 2 serves as a control and was prepared without addition of sulfohydrolase in the reaction mixture.

TABLE 21

| Examples | Sulfohydrolase II, 30 μg/ml (μl) | Water (μl) | Nu-carrageenan (1.4% (w/v) in water) (μl) |
|---|---|---|---|
| Comp. 2 | 0 | 1500 | 1500 |
| 106 | 100 | 1400 | 1500 |
| 107 | 250 | 1250 | 1500 |
| 108 | 500 | 1000 | 1500 |
| 109 | 1000 | 500 | 1500 |

The gel strength and complex viscosity of the incubated samples were measured as shown in Table 22. The measurements in Table 22 are based on a temperature sweep in which the temperature was decreased from 80 to 10° C. and then increased from 10 to 80° C. in sequence. A deformation is applied to the sample at various times during the sweep and the resulting force is measured. The testing was conducted on a Bohlin VOR Rheometer, having a cup-bob system (C14), available from Bohlin Reologi AB, Sjöbo, Sweden. The torque element was 0.24 gcm, with a frequency of 0.5 Hz, and an amplitude of 10+80%.

The force is converted into an elastic and a viscous modulus (G' and G", respectively) and a complex viscosity ($\eta^*$). Gel T. is the temperature where G' crosses G" and is higher than G", when running a sweep where the temperature is decreased. Melt T. is the temperature where G" is higher than G' when running a sweep where the temperature is increased. The gel strength is defined as G' gel or G' melt and is G' obtained at 10° C. The complex viscosity ($\eta^*$) is the viscosity at 10° C.

TABLE 22

| Ex. | Gel T. (° C.) | Melt T. (° C.) | G' gel at 10° C. (Pa) | G' melt at 10° C. (Pa) | $\eta^*$ gel at 10° C. (Pa·s) | $\eta^*$ melt at 10° C. (Pa·s) |
|---|---|---|---|---|---|---|
| Comp. 2 | — | — | — | — | 0.0041 | 0.0346 |
| 106 | — | — | 4 | 0.124 | 0.097 | 0.135 |
| 107 | 25.3 | 35.5 | 38 | 46 | 11.65 | 17.38 |
| 108 | 51.4 | 58.4 | 76 | 69 | 24.54 | 21.868 |
| 109 | 64.4 | 68.1 | 39 | 39 | 12.19 | 12.16 |

Table 22 shows that the gel strength and the complex viscosity increase with increasing enzyme concentration and appears to reach a maximum at approximately 5 μg/ml, after which the gel strength and complex viscosity decrease and become like an alkali treated iota-carrageenan. A certain amount of sulfohydrolase is needed to make a measurable gel, about 1 μg/ml. Low amounts (2.5 μg/ml) of enzyme created a soft gel whereas higher amounts (5 and 10 μg/ml) gave a stronger gel.

EXAMPLE 110 AND COMPARATIVE EXAMPLES 3–5

These Examples are directed to incubations of iota- and nu-carrageenan with partially purified C. crispus extracts.

The iota-carrageenan and nu-carrageenan in Table 24 were both extracted from *Eucheuma denticulatum* (Spinosum), as described below.

Comparative Example 3 serves as a control and involves iota-carrageenan, which is a commercial extract, and which has been treated with calcium hydroxide to fully remove 6-O-sulfate groups and serves as a control.

The nu-carrageenan for Comparative Examples 4–5 and the Examples was extracted in the following manner. Twenty-five (25) grams of freeze-dried and milled Spinosum dispersed in 2.5 liters of 0.125 M KCl. The extraction was at room temperature for 24 hours. Filtration was conducted with Frisenette paperfilters 614–200 mm, available from A. G. Frisenette & sonner APS, Ebeltoft, Denmark. As a result of clogging, the filters needed to be replaced and a total of three filters was used. The liquid was stored in refrigerator (5° C.) overnight. The liquid was then evaporated on Roto-Evaporator RE 120, available from Laboratoriums Technik AG, Flawil, Switzerland, at 2–3 rpm to 50% volume with waterbath at 40° C. The pH was adjusted to approximately 8.0 by adding 6 drops of 1 M NaOH. The carrageenan was precipitated using 100% (v/v) isopropyl alcohol (IPA), available from BP Chemicals Ltd., UK and freeze-dried. The nu-carrageenan was manually broken into pieces having a maximum size of 1 $cm^2$ and dispersed in distilled water at a level of 1% (w/v) of nu-carrageenan. The nu-carrageenan was dialyzed against tap water, using a Spectra/por membrane MWCO 6-8000 or 3500, available from Spectrum Laboratories, Inc., Rancho Dominguez, Calif., USA, until the conductivity in the water was 1.5 μS/cm. The pH of the nu-carrageenan solution was adjusted to 9.3, and then the solution was precipitated and freeze-dried. The freeze-dried composition was milled in a mortar. This extract had both enriched nu-content and a high molecular weight.

Results are also shown for nu-carrageenan incubated with a partially purified 25 sulfohydrolase-containing fraction from *Chondrus crispus*. The purification protocol was generally the same as that shown in the specification, i.e., ammonium sulfate fractionation, phenyl sepharose chromatography, except that Poros HQ chromatography was conducted instead of DEAE Sepharose chromatography. The Poros HQ (4.6×100 mm) chromatography column being available from PerSeptive Biosystems, Foster City, Calif., USA.

The Poros HQ chromatography involved the same buffers as used in the DEAE Sepharose chromatography, but elution was performed as follows and as shown in Table 23:

Buffer A: 50 mM Tris-HCl+10 mM 2-mercaptoethanol pH 7.1

Buffer B: 50 mM Tris-HCl+10 mM 2-mercaptoethanol+1 M NaCl pH 7.1

Flow Rate: 2 ml/min

Fraction Size: 2 ml

TABLE 23

| Time (min) | % of Buffer A | % of Buffer B |
|---|---|---|
| 0 | 100 | 0 |
| 60 | 0 | 100 |

Fractions 28 to 37, which contain sulfohydrolase activity, were pooled and used as the enzyme fraction as described below.

The nu-carrageenan was incubated in a mixture containing: 1.5 ml of 1.4% (w/v, in 50 mM Tris-HCl (pH 7.1)+10 mM 2-mercaptoethanol) of the nu-carrageenan and 1.5 ml of enzyme fraction in 50 mM Tris-HCl (pH 7.1)/10 mM 2-mercaptoethanol.

The reference mixture of Comparative Example 5 was made using a fraction from the phenyl sepharose chromatography that did not display sulfohydrolase activity, i.e., did not release sulfate from the nu-carrageenan. Comparative Example 5 is directed to determining whether gelation was the result of interaction with proteins or whether gelation was the result of interaction with sulfohydrolase.

After 20 hours incubation at 48° C., carrageenan was removed from an aliquot (about 0.2 ml) of the reaction mixture by centrifugation at 3320 g for 1 hr at 30 ° C. in a Microcon-10 unit, available from Amicon Bioseparations, Millipore Corporation, Bedford, Mass., USA, in order to measure the amount of free sulfate released as described in the specification. In contrast, the other measurements (i.e., galactose, 3,6 AG, and viscosity measurements) were directly performed on the reaction mixtures.

The main structural characteristics of nu-carrageenan extracted from *E. denticulatum* (Spinosum), and of the same nu-carrageenan incubated with some protein or with a partially purified enzyme fraction containing both sulfohydrolases from *C. crispus*, are summarized in Table 24.

The viscometric measurements of Table 24 were carried out on the reaction mixture described above with the exception that after incubation at 48° C., the viscosity of the reaction mixture was directly measured using a programmable Brookfield rheometer model DV III, available from Brookfield Engineering Laboratories, Stoughton, Mass., USA, thermostated at 48° C. Measurements were performed with a CP52 spindle for 10 minutes using a shear rate of 120 rpm.

In Table 24, sulfohydrolase activity was assayed by measuring the amount of sulfate released upon incubation of the enzyme extract on the nu carrageenan. The amount of free sulfate present in the filtrate was measured in accordance with the method described in the specification.

TABLE 24

| Ex. | Content | Galactose (mol %) | 3,6-An hydroGal (mol %) | Free Sulfate (% w/w) | Brookfield Viscosity (cP) |
| --- | --- | --- | --- | --- | --- |
| Comp. 3 | iota-carrageenan | 50 | 50 | 0.6 | Too high (gel) |
| Comp. 4 | nu-carrageenan | 68 | 32 | NA | <5 |
| Comp. 5 | nu-carrageenan + protein | 71 | 29 | 0.4 | <5 |
| 110 | nu-carrageenan + partially purified sulfohydrolase I and II | 59 | 41 | 2.3 | 40 |

Table 24 shows that in the presence of sulfohydrolases the sulfate is released and that the 3,6 AG level increases which leads to a gel being formed.

EXAMPLES 111–116 AND
COMPARATIVE EXAMPLES 6–11

These Examples are directed to incubating nu-carrageenan with separate fractions of sulfohydrolase I and II from *C. crispus* to examine the effect on viscosity.

To obtain the sulfohydrolase I and II, the purification procedure generally involved following the protocol described in the specification. The only difference here being that the starting material was 2 kg.

Fractions 21 and 40 were obtained from the same purification experiment, whereas fractions 23 and 48 were obtained from a separate run using the same procedure. Normally, when using 0.6–0.7 kg of seaweed, the sulfohydrolase I elutes first after DEAE Sepharose chromatography and the sulfohydrolase II elutes last, as was the case with fractions 23 and 48. However, in the purification with a batch of 2 kg of seaweed, the order of fractions was once reversed, such that sulfohydrolase II was in fraction 21 and sulfohydrolase I was in fraction 40.

In Table 25, "21+nu", "23+nu", "40+nu", and "48+nu" indicate a mixture of 1 ml of fraction 21, 23, 40, and 48, respectively (in 50 mM Tris-HCl+10 mM 2-mercaptoethanol pH 7.1), 2 ml of MilliQ water, and 3 ml of 1.4% (w/v, in MilliQ water) nu-carrageenan obtained in accordance with method "E" of Examples 39–46, which was incubated for 15 hours at 48° C., and then inactivated at 100° C. for 15 minutes. Controls involved mixtures having the same treatment, except boiled enzyme, i.e., enzyme "@100" as shown in Table 25, was used. "40+nu+21" and "23+nu+48" indicate a mixture of 1 ml of fraction 40 and 23, respectively (in 50 mM Tris-HCl+10 mM 2-mercaptoethanol pH 7.1), 2 ml of MilliQ water, and 3 ml of 1.4% (w/v, in MilliQ water) nu-carrageenan obtained in accordance with method "E" of Examples 39–46, which was incubated for 15 hours at 48° C., then inactivated at 100° C. for 15 minutes, then to which is added 1 ml of fraction 21 and 48, respectively (in 50 mM Tris-HCl+10 mM 2-mercaptoethanol pH 7.1), and then incubated for 6 hours at 48° C.

Results are summarized in Table 25 below.

TABLE 25

| Ex. | Fraction Number | Approx. MW (kDa) | Sulfate Release Y/N | ppm | Viscosity Increase Y/N | cP | T (° C.) | Mol % Iota |
| --- | --- | --- | --- | --- | --- | --- | --- | --- |
| 111 | 21 + nu | 35 (sulfo II) | Y | 139 | Y | 12 | 40 | 92 |
| Comp. 6 | 21 @ 100 + nu | 35 (sulfo II) | | 7 | N | 0.0 | 40 | 77 |
| 112 | 23 + nu | 62 (sulfo I) | Y | 194 | N | 0.3 | 55 | 87 |
| Comp. 7 | 23 @ 100 + nu | 62 (sulfo I) | | 18 | N | 0.0 | 55 | 77 |
| 113 | 40 + nu | 62 (sulfo I) | Y | 69 | N | 0.0 | 40 | 83 |

TABLE 25-continued

| Ex. | Fraction Number | Approx. MW (kDa) | Sulfate Release Y/N | ppm | Viscosity Increase Y/N | cP | T (° C.) | Mol % Iota |
|---|---|---|---|---|---|---|---|---|
| Comp. 8 | 40 @ 100 + nu | 62 (sulfo I) | | 16 | N | 0.0 | 40 | 76 |
| 114 | 48 + nu | 35 (sulfo II) | Y | 93 | Y | 5.6 | 55 | 83 |
| Comp. 9 | 48 @ 100 + nu | 35 (sulfo II) | | 12 | Y | 0.8 | 55 | 76 |
| 115 | 40 + nu + 21 | 62/35 (sulfo I & II) | Y | 105 | Y | 29 | 40 | 95 |
| 116 | 23 + nu + 48 | 62/35 (sulfo I & II) | Y | ? | Y | 12 | 55 | 89 |

Table 25 shows that after incubation of nu-carrageenan with the enzymes, sulfohydrolase I did not increase viscosity of the samples whereas sulfohydrolase II did increase viscosity.

Comparing Examples 113 and 115 shows that incubating the iota-precursor, i.e., nu-carrageenan, with first the random enzyme (sulfohydrolase I) followed by inactivation and thereafter incubation with the processive enzyme (sulfohydrolase II), results in a higher viscosity when compared to using the processive enzyme alone.

The enzymatic modified samples were analyzed by NMR to determine the mode of action of both enzymes. The data indicates that both enzymes are sulfohydrolases, releasing sulfate from the C-6 position of the iota-precursor (nu) and subsequently inducing formation of the 3,6-anhydrobridge.

The gel strength and complex viscosity of the incubated samples was measured as shown in Table 28. In Table 28, the sample for Comparative Example 10 was made by dispersing 0.7% (w/v) of the iota-carrageenan listed in Table 1 in 20 ml of ion exchanged water containing 2 ml of 0.5% (w/v) of potassium chloride and 2 ml of 0.25% (w/v) of calcium chloride. The solution was heated to 80° C. and evaporated to 5 ml. The sample for Comparative Example 11 was nu-carrageenan without enzyme.

The measurements in Table 28 are based on the methods described in Tables 26 and 27. Table 26 shows the method for determining the gelling profile, with a start temperature of 80° C. Table 27 shows the method for deter mining the melting profile, with a start temperature of 10° C. Unless otherwise noted in Tables 26–27, measurements were conducted using a Bohlin VOR Rheometer, as described in Examples 106–109 and Comparative Example 2.

TABLE 26

| Mode | Ramp/ Hold | T (° C.) | Time (s) | Sample Int. (s) | Freq. (Hz) | Amp. (%) |
|---|---|---|---|---|---|---|
| oscillation | ramp | 61 | 1140 | 20 | 0.5 | 80 |
| oscillation | ramp | 10 | 3060 | 20 | 0.5 | 10 |

TABLE 27

| Mode | Ramp/ Hold | T (° C.) | Time (s) | Sample Int. (s) | Freq. (Hz) | Amp. (%) |
|---|---|---|---|---|---|---|
| oscillation | ramp | 58 | 2280 | 20 | 0.5 | 10 |
| oscillation | ramp | 80 | 1320 | 20 | 0.5 | 80 |

TABLE 28

| Ex. | component | Gel T. (° C.) | Melt T. (° C.) | $\eta^*$ at 40° C. (cP) | $\eta^*$ at 10° C. (cP) | G' (Pa) |
|---|---|---|---|---|---|---|
| Comp. 10 | iota | 60.8 | 65.3 | 8372 | 12287 | 38.4 |
| 111 | 21 + nu | 37.1 | 39.2 | 42 | 15120 | 47.3 |
| 113 | 40 + nu | 22.5 | 28.8 | 4.3 | 6557 | 20.6 |
| 115 | 40 + nu + 21 | 49.4 | 56.8 | 3979 | 13560 | 42.4 |
| Comp. 11 | nu | — | — | — | — | — |

As shown in Table 28, the enzyme preparations were able to influence the gelling and melting temperature of the polymer. The viscosity of the enzymatic modified polymer was lower than the traditional iota carrageenan. The difference in viscosity and gelling point might be caused by ionic and concentration effects and can be optimized for the enzymatic prepared samples.

While the invention has been described in connection with certain preferred embodiments so that aspects thereof may be more fully understood and appreciated, it is not intended to limit the invention to these particular embodiments. On the contrary, it is intended to cover all alternatives, modifications and equivalents as may be included within the scope of the invention as defined by the appended claims.

What is claimed is:

1. An isolated protein comprising an amino acid sequence comprising SEQ ID NO: 23.

2. An isolated protein which modifies residues containing sulfur present in hydrocolloids comprising an amino acid sequence which has at least about 20% homology with SEQ ID NO: 23.

3. The isolated protein of claim 2, wherein the amino acid sequence has at least about 50% homology with SEQ ID NO: 23.

4. The isolated protein of claim 2, wherein the amino acid sequence has at least about 80% homology with SEQ ID NO: 23.

5. The isolated protein of claim 2, wherein the protein removes ester-sulfate groups present in hydrocolloids.

6. The isolated protein of claim 2, wherein the protein hydrolyzes sulfate ester bonds present in hydrocolloids.

7. A product made by incubating a sulfated compound with a solution having a protein content consisting essentially of a sulfohydrolase from seaweed which removes sulfate groups processively.

8. A product made by incubating a sulfated compound with a solution having a protein content consisting essentially of a sulfohydrolase from seaweed which removes sulfate groups randomly.

9. A product made by:

incubating a sulfated compound with a first solution having a protein content consisting essentially of a first sulfohydrolase from seaweed which removes sulfate groups randomly, to form an intermediate compound; and subsequently incubating said intermediate compound with a second solution having a protein content consisting essentially of a second sulfohydrolase from seaweed which removes sulfate groups processively.

* * * * *